US009089372B2

(12) United States Patent
O'Neil et al.

(10) Patent No.: US 9,089,372 B2
(45) Date of Patent: Jul. 28, 2015

(54) PEDICULAR FACET FUSION SCREW WITH PLATE

(75) Inventors: Michael O'Neil, West Barnstable, MA (US); John R. Hawkins, Cumberland, RI (US); Michael A. Fisher, Grayson, GA (US); Robert A. Hart, Portland, OR (US); Richard Fessler, Winnetka, IL (US); Robert D. Labrom, Taringa (AU); Hassan A. Serhan, South Easton, MA (US); Shawn D. Stad, Fall River, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 906 days.

(21) Appl. No.: 12/834,417

(22) Filed: Jul. 12, 2010

(65) Prior Publication Data

US 2012/0010662 A1    Jan. 12, 2012

(51) Int. Cl.
*A61B 17/04* (2006.01)
*A61B 17/86* (2006.01)
*A61F 2/08* (2006.01)
*A61B 17/70* (2006.01)
*A61B 17/80* (2006.01)

(52) U.S. Cl.
CPC ......... *A61B 17/7064* (2013.01); *A61B 17/8038* (2013.01); *A61B 17/8605* (2013.01); *A61B 17/8625* (2013.01); *A61B 17/8695* (2013.01); *A61B 17/8061* (2013.01)

(58) Field of Classification Search
CPC ............. A61B 17/7064; A61B 17/864; A61B 17/8625; A61B 17/863
USPC ................. 606/246, 264–272, 300–321, 247
See application file for complete search history.

(56) References Cited

U.S. PATENT DOCUMENTS

| 673,009 A | 4/1901 | Poulson |
| 3,934,444 A | 1/1976 | Simons |
| 4,011,602 A | 3/1977 | Rybicki et al. |
| 4,263,904 A | 4/1981 | Judet et al. |

(Continued)

FOREIGN PATENT DOCUMENTS

| EP | 0502698 | 9/1992 |
| EP | 0856293 A1 | 8/1998 |

(Continued)

OTHER PUBLICATIONS

Akira Igarashi, M.D., et al., "Inflammatory Cytokines Released from the Facet Joint Tissue in Degenerative Lumbar Spinal Disorders", Spine vol. 29, No. 19, pp. 2091-2095, Lippincott Williams & Wilkins, Inc., Oct. 1, 2004.

(Continued)

*Primary Examiner* — Ellen C Hammond
*Assistant Examiner* — Christina Negrellirodrigue
(74) *Attorney, Agent, or Firm* — Nutter McClennen & Fish LLP

(57) ABSTRACT

Spinal implants and methods for spinal stabilization and/or fusion are provided. Exemplary implants described herein can be configured for delivery to a facet joint to stabilize and/or fuse the facet joint, and can optionally be anchored within the pedicle for added fixation. The implant can optionally include a fusion-promoting bioactive material thereby providing a single device capable of spinal stabilization and/or fusion. Furthermore, a method of placing such an implant within a facet joint is provided.

26 Claims, 17 Drawing Sheets

(56) References Cited

U.S. PATENT DOCUMENTS

| | | |
|---|---|---|
| 4,576,534 A | 3/1986 | Barth et al. |
| 4,590,928 A | 5/1986 | Hunt et al. |
| 4,858,603 A | 8/1989 | Clemow et al. |
| 4,878,794 A | 11/1989 | Potucek |
| 4,898,186 A | 2/1990 | Ikada et al. |
| 4,927,421 A | 5/1990 | Goble et al. |
| 4,961,740 A | 10/1990 | Ray et al. |
| 4,988,351 A | 1/1991 | Paulos et al. |
| 5,059,193 A | 10/1991 | Kuslich |
| 5,100,405 A | 3/1992 | McLaren |
| 5,129,904 A | 7/1992 | Illi |
| 5,152,303 A | 10/1992 | Allen |
| 5,156,616 A | 10/1992 | Meadows et al. |
| 5,169,400 A | 12/1992 | Muhling et al. |
| 5,180,388 A | 1/1993 | DiCarlo |
| 5,275,601 A | 1/1994 | Gogolewski et al. |
| 5,314,427 A | 5/1994 | Goble et al. |
| 5,364,400 A | 11/1994 | Rego, Jr. et al. |
| 5,403,136 A | 4/1995 | Mathys et al. |
| 5,409,486 A | 4/1995 | Reese |
| 5,443,509 A | 8/1995 | Boucher et al. |
| 5,456,685 A | 10/1995 | Huebner |
| 5,470,334 A | 11/1995 | Ross et al. |
| 5,487,744 A | 1/1996 | Howland |
| D368,777 S | 4/1996 | Goble et al. |
| 5,527,312 A | 6/1996 | Ray |
| 5,545,163 A | 8/1996 | Miller et al. |
| 5,558,674 A | 9/1996 | Heggeness et al. |
| D374,286 S | 10/1996 | Goble et al. |
| D374,287 S | 10/1996 | Goble et al. |
| D374,482 S | 10/1996 | Goble et al. |
| 5,562,672 A | 10/1996 | Huebner et al. |
| 5,571,104 A | 11/1996 | Li |
| 5,571,139 A | 11/1996 | Jenkins, Jr. |
| 5,613,968 A | 3/1997 | Lin |
| 5,645,547 A | 7/1997 | Coleman |
| 5,681,311 A | 10/1997 | Foley et al. |
| 5,697,929 A | 12/1997 | Mellinger |
| 5,743,912 A | 4/1998 | Lahille et al. |
| 5,743,914 A | 4/1998 | Skiba |
| 5,840,078 A | 11/1998 | Yerys |
| 5,871,486 A | 2/1999 | Huebner et al. |
| 5,885,300 A | 3/1999 | Tokuhashi et al. |
| 5,888,228 A | 3/1999 | Knothe et al. |
| 5,925,047 A | 7/1999 | Errico et al. |
| 5,947,969 A | 9/1999 | Errico et al. |
| 5,951,560 A | 9/1999 | Simon et al. |
| 5,964,761 A | 10/1999 | Kambin |
| 5,968,047 A | 10/1999 | Reed |
| 5,989,255 A | 11/1999 | Pepper et al. |
| 6,007,539 A | 12/1999 | Kirsch et al. |
| 6,030,162 A | 2/2000 | Huebner |
| 6,045,554 A | 4/2000 | Grooms et al. |
| 6,048,343 A | 4/2000 | Mathis et al. |
| 6,080,157 A | 6/2000 | Cathro et al. |
| 6,096,060 A | 8/2000 | Fitts et al. |
| 6,099,529 A | 8/2000 | Gertzman et al. |
| 6,126,663 A | 10/2000 | Hair |
| 6,162,225 A | 12/2000 | Gertzman et al. |
| 6,210,442 B1 | 4/2001 | Wing et al. |
| 6,214,007 B1 | 4/2001 | Anderson |
| 6,214,012 B1 | 4/2001 | Karpman et al. |
| 6,277,149 B1 | 8/2001 | Boyle et al. |
| 6,280,443 B1 | 8/2001 | Gu et al. |
| 6,283,973 B1 | 9/2001 | Hubbard et al. |
| 6,383,187 B2 | 5/2002 | Tormala et al. |
| 6,402,757 B1 | 6/2002 | Moore, III et al. |
| 6,461,373 B2 | 10/2002 | Wyman et al. |
| 6,464,706 B1 | 10/2002 | Winters |
| 6,485,518 B1 | 11/2002 | Cornwall et al. |
| 6,488,683 B2 | 12/2002 | Lieberman |
| 6,506,192 B1 | 1/2003 | Gertzman et al. |
| 6,524,316 B1 | 2/2003 | Nicholson et al. |
| 6,527,773 B1 | 3/2003 | Lin et al. |
| 6,540,747 B1 | 4/2003 | Marino |
| 6,565,572 B2 | 5/2003 | Chappius |
| 6,569,186 B1 | 5/2003 | Winters et al. |
| 6,575,976 B2 | 6/2003 | Grafton |
| 6,585,518 B1 | 7/2003 | Jenkins et al. |
| 6,589,245 B1 | 7/2003 | Weiler et al. |
| 6,629,977 B1 | 10/2003 | Wolf |
| 6,641,583 B2 | 11/2003 | Shluzas et al. |
| 6,648,893 B2 | 11/2003 | Dudasik |
| 6,666,868 B2 | 12/2003 | Fallin |
| 6,685,706 B2 | 2/2004 | Padget et al. |
| 6,723,095 B2 | 4/2004 | Hammerslag |
| 6,730,093 B2 | 5/2004 | Saint Martin |
| 6,808,526 B1 | 10/2004 | Magerl et al. |
| 6,811,567 B2 | 11/2004 | Reiley |
| 6,921,402 B2 | 7/2005 | Contiliano et al. |
| 6,923,814 B1 | 8/2005 | Hildebrand et al. |
| 6,945,975 B2 | 9/2005 | Dalton |
| 6,966,930 B2 | 11/2005 | Arnin et al. |
| 6,976,818 B2 | 12/2005 | Levey et al. |
| 6,979,333 B2 | 12/2005 | Hammerslag |
| 6,981,974 B2 | 1/2006 | Berger |
| 7,056,341 B2 | 6/2006 | Crozet |
| 7,090,675 B2 | 8/2006 | Songer |
| 7,101,398 B2 | 9/2006 | Dooris et al. |
| 7,108,697 B2 | 9/2006 | Mingozzi et al. |
| 7,291,149 B1 | 11/2007 | Michelson |
| 7,410,789 B2 | 8/2008 | Schlosser et al. |
| 7,491,221 B2 | 2/2009 | David |
| 7,699,878 B2 | 4/2010 | Pavlov et al. |
| 7,708,761 B2 | 5/2010 | Peterson |
| 7,794,484 B2 * | 9/2010 | Stone et al. .................. 606/329 |
| 7,799,057 B2 | 9/2010 | Hudgins et al. |
| 7,909,826 B2 | 3/2011 | Serhan et al. |
| 8,123,749 B2 | 2/2012 | Serhan et al. |
| 8,142,503 B2 * | 3/2012 | Malone ...................... 623/16.11 |
| 2001/0029375 A1 | 10/2001 | Betz et al. |
| 2002/0042615 A1 | 4/2002 | Graf et al. |
| 2002/0151895 A1 | 10/2002 | Soboleski et al. |
| 2002/0177898 A1 | 11/2002 | Crozet |
| 2002/0183747 A1 | 12/2002 | Jao et al. |
| 2002/0193795 A1 * | 12/2002 | Gertzbein et al. .............. 606/61 |
| 2003/0032960 A1 | 2/2003 | Dudasik |
| 2003/0040746 A1 | 2/2003 | Mitchell et al. |
| 2003/0125740 A1 | 7/2003 | Khanna |
| 2003/0153921 A1 | 8/2003 | Stewart et al. |
| 2004/0006342 A1 | 1/2004 | Altarac et al. |
| 2004/0082956 A1 | 4/2004 | Baldwin et al. |
| 2004/0087948 A1 | 5/2004 | Suddaby |
| 2004/0111093 A1 | 6/2004 | Chappuis |
| 2004/0127906 A1 | 7/2004 | Culbert et al. |
| 2004/0127989 A1 | 7/2004 | Dooris et al. |
| 2004/0143267 A1 | 7/2004 | Fallin |
| 2004/0143268 A1 | 7/2004 | Falahee |
| 2004/0167520 A1 | 8/2004 | Zucherman et al. |
| 2004/0186475 A1 | 9/2004 | Falahee |
| 2004/0225292 A1 | 11/2004 | Sasso et al. |
| 2004/0225360 A1 | 11/2004 | Malone |
| 2004/0230192 A1 | 11/2004 | Graf |
| 2004/0249376 A1 | 12/2004 | Hammerslag |
| 2004/0254575 A1 | 12/2004 | Obenchain et al. |
| 2004/0260296 A1 | 12/2004 | Kaiser et al. |
| 2004/0260298 A1 * | 12/2004 | Kaiser et al. ..................... 606/72 |
| 2005/0015060 A1 | 1/2005 | Sweeney |
| 2005/0027293 A1 | 2/2005 | LeHuec et al. |
| 2005/0038434 A1 | 2/2005 | Mathews |
| 2005/0055026 A1 * | 3/2005 | Biedermann et al. ........... 606/73 |
| 2005/0113929 A1 | 5/2005 | Cragg et al. |
| 2005/0119657 A1 | 6/2005 | Goldsmith |
| 2005/0124993 A1 | 6/2005 | Chappuis |
| 2005/0149030 A1 | 7/2005 | Serhan et al. |
| 2005/0165399 A1 | 7/2005 | Michelson |
| 2005/0177240 A1 | 8/2005 | Blain |
| 2005/0192572 A1 | 9/2005 | Abdelgany et al. |
| 2005/0192580 A1 | 9/2005 | Dalton |
| 2005/0197660 A1 | 9/2005 | Haid et al. |
| 2005/0197700 A1 | 9/2005 | Boehm et al. |
| 2005/0216016 A1 | 9/2005 | Contiliano et al. |
| 2005/0222681 A1 | 10/2005 | Richley et al. |
| 2005/0228384 A1 | 10/2005 | Zucherman et al. |

(56) References Cited

U.S. PATENT DOCUMENTS

| | | |
|---|---|---|
| 2005/0234459 A1 | 10/2005 | Falahee et al. |
| 2005/0234551 A1 | 10/2005 | Fallin et al. |
| 2005/0234552 A1 | 10/2005 | Reiley |
| 2005/0240188 A1 | 10/2005 | Chow et al. |
| 2005/0251256 A1 | 11/2005 | Reiley |
| 2005/0261770 A1 | 11/2005 | Kuiper et al. |
| 2005/0267480 A1 | 12/2005 | Suddaby |
| 2005/0273110 A1 | 12/2005 | Boehm et al. |
| 2006/0004358 A1 | 1/2006 | Serhan et al. |
| 2006/0004367 A1 | 1/2006 | Alamin et al. |
| 2006/0004448 A1 | 1/2006 | Casey |
| 2006/0004449 A1 | 1/2006 | Goble et al. |
| 2006/0004451 A1 | 1/2006 | Goble et al. |
| 2006/0009847 A1 | 1/2006 | Reiley |
| 2006/0009848 A1 | 1/2006 | Reiley |
| 2006/0015105 A1 | 1/2006 | Warren et al. |
| 2006/0030948 A1 | 2/2006 | Manrique et al. |
| 2006/0036243 A1 | 2/2006 | Sasso et al. |
| 2006/0036323 A1 | 2/2006 | Carl et al. |
| 2006/0041311 A1 | 2/2006 | McLeer |
| 2006/0052785 A1 | 3/2006 | Augostino et al. |
| 2006/0064099 A1 | 3/2006 | Pavlov et al. |
| 2006/0085068 A1 | 4/2006 | Barry |
| 2006/0089646 A1 | 4/2006 | Bonutti |
| 2006/0095036 A1 | 5/2006 | Hammerslag |
| 2006/0095040 A1 | 5/2006 | Schlienger et al. |
| 2006/0106381 A1 | 5/2006 | Ferree et al. |
| 2006/0111179 A1 | 5/2006 | Inamura |
| 2006/0111779 A1 | 5/2006 | Petersen |
| 2006/0111782 A1 | 5/2006 | Petersen |
| 2006/0122609 A1 | 6/2006 | Mirkovic et al. |
| 2006/0149239 A1 | 7/2006 | Winslow et al. |
| 2006/0149254 A1 | 7/2006 | Lauryssen et al. |
| 2006/0149272 A1 | 7/2006 | Winslow et al. |
| 2006/0149289 A1 | 7/2006 | Winslow et al. |
| 2006/0149373 A1 | 7/2006 | Winslow et al. |
| 2006/0149374 A1 | 7/2006 | Winslow et al. |
| 2006/0178743 A1 | 8/2006 | Carter |
| 2006/0190081 A1 | 8/2006 | Kraus et al. |
| 2006/0200137 A1 | 9/2006 | Soboleski et al. |
| 2006/0217713 A1 | 9/2006 | Serhan et al. |
| 2006/0217714 A1 | 9/2006 | Serhan et al. |
| 2006/0217715 A1* | 9/2006 | Serhan et al. .......... 606/61 |
| 2006/0235388 A1 | 10/2006 | Justis et al. |
| 2006/0235391 A1 | 10/2006 | Sutterlin |
| 2006/0241597 A1 | 10/2006 | Mitchell et al. |
| 2006/0241758 A1 | 10/2006 | Peterman et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0264953 A1 | 11/2006 | Falahee |
| 2006/0271054 A1 | 11/2006 | Sucec et al. |
| 2006/0276790 A1 | 12/2006 | Dawson et al. |
| 2006/0276801 A1 | 12/2006 | Yerby et al. |
| 2006/0293658 A1 | 12/2006 | Sharim |
| 2007/0016191 A1 | 1/2007 | Culbert et al. |
| 2007/0016195 A1 | 1/2007 | Winslow et al. |
| 2007/0016196 A1 | 1/2007 | Winslow et al. |
| 2007/0016218 A1 | 1/2007 | Winslow et al. |
| 2007/0055236 A1 | 3/2007 | Hudgins et al. |
| 2007/0055373 A1 | 3/2007 | Hudgins et al. |
| 2007/0073290 A1 | 3/2007 | Boehm |
| 2007/0118132 A1 | 5/2007 | Culbert et al. |
| 2007/0135814 A1 | 6/2007 | Farris |
| 2007/0233093 A1 | 10/2007 | Falahee |
| 2007/0233113 A1 | 10/2007 | Kaelblein et al. |
| 2007/0250166 A1 | 10/2007 | McKay |
| 2008/0086131 A1 | 4/2008 | Daly et al. |
| 2008/0103512 A1 | 5/2008 | Gately |
| 2008/0177334 A1 | 7/2008 | Stinnette |
| 2008/0234758 A1 | 9/2008 | Fisher et al. |
| 2008/0255618 A1* | 10/2008 | Fisher et al. .......... 606/247 |
| 2008/0255622 A1 | 10/2008 | Mickiewicz et al. |
| 2008/0255666 A1 | 10/2008 | Fisher et al. |
| 2008/0275507 A1 | 11/2008 | Triplett et al. |
| 2008/0306537 A1 | 12/2008 | Culbert |
| 2008/0306555 A1 | 12/2008 | Patterson et al. |
| 2008/0319483 A1 | 12/2008 | Triplett et al. |
| 2008/0319484 A1 | 12/2008 | Fauth |
| 2008/0319485 A1 | 12/2008 | Fauth et al. |
| 2008/0319488 A1 | 12/2008 | Helgerson |
| 2008/0319489 A1 | 12/2008 | Triplett |
| 2009/0012566 A1 | 1/2009 | Fauth |
| 2009/0036926 A1 | 2/2009 | Hestad |
| 2009/0036986 A1 | 2/2009 | Lancial et al. |
| 2009/0099602 A1 | 4/2009 | Aflatoon |
| 2009/0105716 A1 | 4/2009 | Barrus |
| 2009/0112269 A1* | 4/2009 | Lieberman et al. .......... 606/301 |
| 2009/0125066 A1 | 5/2009 | Kraus et al. |
| 2009/0138053 A1 | 5/2009 | Assell et al. |
| 2009/0192551 A1* | 7/2009 | Cianfrani et al. .......... 606/301 |
| 2009/0192553 A1 | 7/2009 | Maguire et al. |
| 2009/0270927 A1 | 10/2009 | Perrow et al. |
| 2009/0312763 A1 | 12/2009 | McCormack et al. |
| 2010/0016903 A1* | 1/2010 | Matityahu et al. .......... 606/301 |
| 2010/0042167 A1* | 2/2010 | Nebosky et al. .......... 606/315 |
| 2010/0094349 A1 | 4/2010 | Hammer et al. |
| 2012/0010699 A1 | 1/2012 | Vesely |

FOREIGN PATENT DOCUMENTS

| | | |
|---|---|---|
| EP | 1210914 A1 | 6/2002 |
| EP | 1248568 A2 | 10/2002 |
| EP | 1452146 A1 | 9/2004 |
| EP | 1585449 A1 | 10/2005 |
| EP | 1813216 A1 | 8/2007 |
| JP | 11-501235 A | 2/1999 |
| JP | 11-504227 A | 4/1999 |
| JP | 2004-305262 A | 11/2004 |
| JP | 2007-502152 A | 2/2007 |
| WO | 96/08206 A1 | 3/1996 |
| WO | WO-0041636 A1 | 7/2000 |
| WO | WO-0062684 A1 | 10/2000 |
| WO | WO-0141681 A1 | 6/2001 |
| WO | WO-0234120 A2 | 5/2002 |
| WO | WO-03007829 A1 | 1/2003 |
| WO | WO-2004043278 A1 | 5/2004 |
| WO | WO-2004100808 A1 | 11/2004 |
| WO | WO-2004110288 A2 | 12/2004 |
| WO | WO-2005004733 A1 | 1/2005 |
| WO | 2005/018684 A2 | 3/2005 |
| WO | WO-2005042036 A2 | 5/2005 |
| WO | WO-2005060845 A1 | 7/2005 |
| WO | WO-2005076974 A2 | 8/2005 |
| WO | WO-2005097005 A1 | 10/2005 |
| WO | WO-2006002684 A1 | 1/2006 |
| WO | WO-2006007739 A1 | 1/2006 |
| WO | WO-2006009855 A2 | 1/2006 |
| WO | WO-2006047707 A2 | 5/2006 |
| WO | WO-2006057943 A2 | 6/2006 |
| WO | WO-2006065774 A1 | 6/2006 |
| WO | WO-2006086241 A2 | 8/2006 |
| WO | WO-2006096803 A2 | 9/2006 |
| WO | WO-2006116119 A2 | 11/2006 |
| WO | WO-2007019710 A1 | 2/2007 |
| WO | WO-2007041698 A1 | 4/2007 |
| WO | WO-2007047711 A2 | 4/2007 |
| WO | WO-2007063399 A1 | 6/2007 |
| WO | WO-2007075454 A1 | 7/2007 |
| WO | WO-2007120903 A2 | 10/2007 |
| WO | WO-2007127610 A1 | 11/2007 |
| WO | 2008/011495 A2 | 1/2008 |
| WO | WO-2008124196 A2 | 10/2008 |
| WO | WO-2008153732 A1 | 12/2008 |
| WO | WO-2009018220 A1 | 2/2009 |
| WO | WO-2009067486 A2 | 5/2009 |
| WO | WO-2009138053 A1 | 11/2009 |

OTHER PUBLICATIONS

Albert C. Schmidt, M.D., et al., "Lumbar Fusion Using Facet Inlay Grafts", Southern Medical Journal, vol. 68, No. 2., Feb. 1975.
Andrew V. Slucky, M.D., et al., "Less Invasive Posterior Fixation Method Following Transforaminal Lumbar Interbody Fusion: a

(56) References Cited

OTHER PUBLICATIONS

Biomechanical Analysis", The Spine Journal 6 (2006) 78-85.

Anil Sethi, et al., "Transforaminal Lumbar Interbody Fusion Using Unilateral Pedicle Screws and a Translaminar Screw", Eur Spine J (2009) 18:430-434 DOI 10.1007/s00586-008-0825-4, Mar. 2009.

U.S. Appl. No. 12/834,397 for "Pedicular Facet Fusion Screw With Plate" filed Jul. 12, 2010.

U.S. Appl. No. 12/834,417 for "Pedicular Facet Fusion Screw With Plate" filed Jul. 12, 2010.

Brain W. Su, MD, et al. "An Anatomic and Radiographic Study of Lumbar Facets Relevant to Percutaneous Transfacet Fixation", Spine vol. 34, No. 11, pp. E384-E390, 2009, Lippincott Williams & Wilkins.

Brian P. Beaubien, BME, et al., "In Vitro, Biomechanical Comparison of an Anterior Lumbar Interdody Fusion with an Anteriorly Placed, Low-Profile Lumbar Plate and Posteriorly Placed Pedicle Screws or Translaminar Screws", Spine vol. 30, No. 16, pp. 1846-1851, © 2005, Lippincott Williams & Wilkins, Inc.

Brian P. Beaubien, BME, et al., "Posterior Augmentation of an Anterior Lumbar Interbody Fusion", Spine vol. 29, No. 19, pp. E406-E412, © 2004, Lippincott Williams & Wilkins, Inc.

Ch. D. Ray, "Transfacet Decompression with Dowel Fixation: a New Technique for Lumbar Lateral Spinal Stenosis", Acta Neurochirurgica, Suppl. 43, 48-54 (1988) © by Springer-Verlag 1988.

D.A. McQueen, M.D. et al., "Knee Arthrodesis with the Wichita Fusion Nail", Clinical Orthopaedics and Related Research, No. 446, pp. 132-139, © 2006 Lippincott Williams & Wilkins.

D.Grob et al., Translaminar screw fixation in the lumbar spine: technique, indications, results, Eur Spine J (1998) vol. 7:178-186, © Springer-Verlag 1998.

David W. Polly, Jr., M.D., et al. "Surgical Treatment for the Painful Motion Segment", Spine vol. 30, No. 16S, pp. S44-S51, © 2005, Lippincott Williams & Wilkins, Inc.

Douglas Burton, M.D., et al., "Biomechanical Analysis of Posterior Fixation Techniques in a 360° Arthrodesis Model", Spine vol. 30, No. 24, pp. 2765-2771, © 2005, Lippincott Williams & Wilkins, Inc.

Frank Kandziora, M.D., et al., "Biomechanical Testing of the Lumbar Facet Interference Screw", Spine vol. 30, No. 2, pp. E34-E39, © 2005, Lippincott Williams & Wilkins, Inc.

Frank M. Phillips, M.D., "Effect of Supplemental Translaminar Facet Screw Fixation on the Stability of Stand-Alone Anterior Lumbar Interbody Fusion Cages Under Physiologic Compressive Preloads", Spine vol. 29, No. 16, pp. 1731-1736, , Lippincott Williams & Wilkins, Inc © 2004, Augus.

Frank M. Phillips, M.D., "Effect of Supplemental Translaminar Facet Screw Fixation on the Stability of Stand-Alone Anterior Lumbar Interbody Fusion Cages Under Physiologic Compressive Preloads", Spine vol. 29, No. 16, pp. 1731-1736, Lippincott Williams & Wilkins, Inc., Aug. 2004.

Frank M. Phillips, M.D., et al., "Radiographic Criteria for Placement of Translaminar Facet Screws", The Spine Journal 4 (2004) 465-467.

Hans Trouillier, et al., "A Prospective Morphological Study of Facet Joint Integrity Following Intervertebral Disc Replacement with the CHARITE™ Artificial Disc", Eur Spine J. (2006) vol. 15: 174-182 DOI 10.1007/s00586-005-1010-7, Jul. 2005.

Harri Pihajamäki, et al., "Tissue Response to Polyglycolide, Polydioxanone, Polylevolactide, and Metallic Pins in Cancellous Bone: An Experimental Study on Rabbits", Journal of Orthopaedic Research, Aug. 2006.

International Search Report and Report Opinion dated Sep. 16, 2008 for PCT/US08/59889.

International Search Report and Written Opinion dated Sep. 24, 2008 for PCT/US08/59866.

International Search Report and Written Opinion dated Jul. 25, 2008 for PCT/US08/50194.

Jee-Soo Jang, M.D., et. al., "Clinical Analysis of Percutaneous Facet Screw Fixation after Anterior Lumbar Interbody Fusion", J Neurosurg: Spine 3:40-46, Jul. 2005.

Jee-Soo Jang, M.D., et. al., "Minimally Invasive Transforaminal Lumbar Interbody Fusion with Ipsilateral Pedicle Screw and Contralateral Facet Screw Fixation", J Neurosurg: Spine 3:218-223, Sep. 2005.

John W. Klekamp, et. al., "Cervical Transfacet Versus Lateral Mass Screws: A Biomechanical Comparison", Journal of Spinal Disorders, vol. 13, No. 6, pp. 515-518, 2000, Lippincott Williams & Wilkins, Inc., Philadelphia: Dec. 2000.

Langston T, Holly, M.D., et al., "Percutaneous Placement of Posterior Cervical Screws Using Three-Dimensional Fluoroscopy", Spine vol. 31, No. 5, pp. 536-540, © 2006, Lippincott Williams & Wilkins, Inc.

Lisa A. Ferrara, et al., "A Biomechanical Comparison of Facet Screw Fixation and Pedicle Screw Fixation", Spine vol. 28, No. 12, pp. 1226-1234, Lippincott Williams & Wilkins, Jun. 15, 2003.

Matthijs R. Krijnen, M.D., et al, "Does Bioresorbable Cage Material Influence Segment Stability in Spinal Interbody Fusion?" Clinical Orthopaedics and Related Research, No. 448, pp. 33-38 © 206 Lippincott Williams & Wilkins.

Natalie M. Best, et al., "Efficacy of Translaminar Facet Screw Fixation in Circumferential Interbody Fusions as Compared to Pedicle Screw Fixation", J Spinal Disord Tech, vol. 19, No. 2, Apr. 2006.

Neil Duggal, M.D., et al., "Unilateral Cervical Facet Dislocation: Biomechanics of Fixation", Spine vol. 30, No. 7, pp. E164-E168, © 2005, Lippincott Williams & Wilkins, Inc.

Nicola C. Gries, et al., "Early Histologic Changer in Lower Lumbar Discs and Facet joints and their Correlation", Eur Spine J (2000) 9:23-29 © Springer-Verlag 2000, Feb. 2000.

Philipp Schleicher, M.D., et al., "Biomechanical Evaluation of Different Asymmetrical Posterior Stabilization Methods for Minimally Invasive Transforaminal Lumbar Interbody Fusion", J. Neurosurg: Spine, vol. 9, Oct. 2008.

Sung-Min Kim, M.D., et al., "A Biomechanical Comparison of Supplementary Posterior Translaminar Facet and Transfacetopedicular Screw Fixation after Anterior Lumbar Interbody Fusiion", J Neurosurg (Spine 1) 1:101-107, Jul. 2004.

Th.-M. Markwalder, et al, "Translaminar Screw Fixation in Lumbar Spine Pathology", Acta Neurochir (Wien) (1989) 99: 58-60.

Thomas Tischer, et al., "Detailed Pathological Changes of Human Lumbar Facet joints L1-L5 in Elderly Individuals", Eur Spine J Mar. 2006;15(3):308-15, Epub July, vol. 15, 2005.

Yasuaki Tokuhashi, M.D., et al., "C1-C2 Intra-articular Screw Fixation for Atlantoaxial Posterior Stabilization", Spine vol. 25, No. 3, pp. 337-241, Lippincott Williams & Wilkins, Inc., Feb. 1, 2000.

Youn-Kwan Park, M.D., "Facet Fusion in the Lumbosacral Spine: A 2-year Follow-Up Study", vol. 51, No. 1, Jul. 2002.

Youssef masharawi, PhD, BPT, et al., "Facet Tropism and Interfacet Shape in the Thoracolumbar Vertebrae", Spine vol. 30, No. 11, pp. E281-E292, © 2005, Lippincott Williams & Wilkins, Inc., Aug. 15, 2004.

Youssef Masharawi, PhD, et al., "Facet Orientation in the Thoracolumbar Spine", Spine vol. 29, No. 16, pp. 1755-1763, © 2004, Lippincott Williams & Wilkins, Inc.

Yukihiro Kai, M.D., et al., "Posterior Lumbar Interbody Fusion Using Local Facet Joint Autograft and Pedicle Screw Fixation", Spine vol. 29, No. 1, pp. 41-46, Lippincott Williams & Wilkins, Inc., Jan. 1, 2004.

Extended European Search Report issued Nov. 7, 2011 for Application No. 08745489.8 (4 pages).

International Search Report and Written Opinion mailed Nov. 9, 2011 for Application No. PCT/US2011/042335 (16 pages).

International Preliminary Report on Patentability mailed Jan. 24, 2013 for Application No. PCT/US2011/042335 (13 Pages).

Extended European Search Report for Application No. 11807276.8 issued Nov. 25, 2014 (6 pages).

European Office Action for Application No. 08745489.8, issued Mar. 27, 2014 (6 pages).

Japanese Office Action for Application No. 2013-519699, issued Jan. 6, 2015 (7 pages).

* cited by examiner

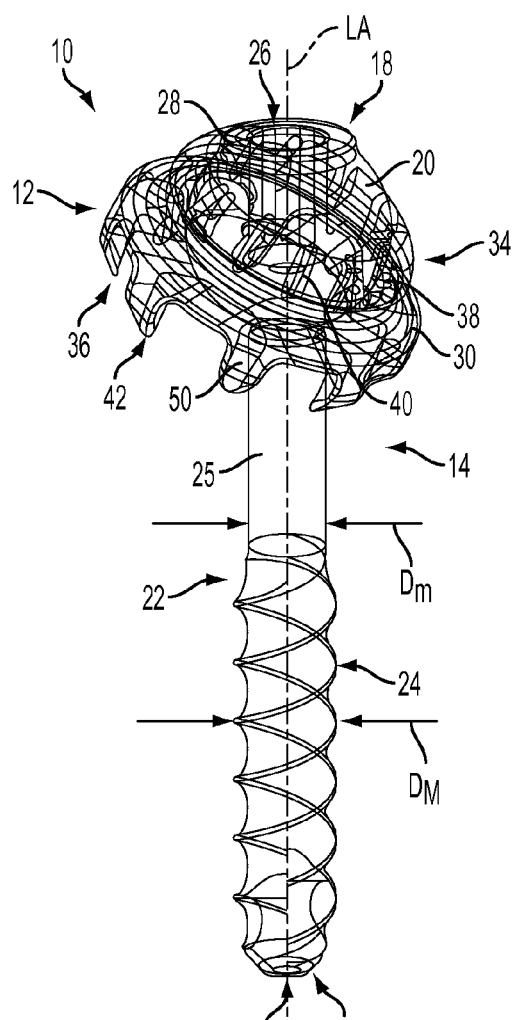
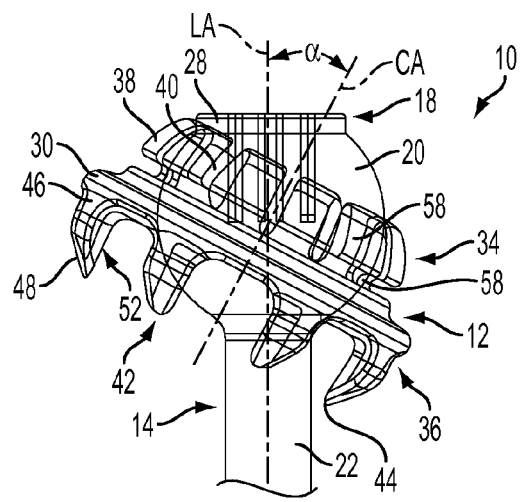
FIG. 2A
FIG. 2B

PEDICULAR FACET FUSION SCREW WITH PLATE

FIELD

The present invention relates to methods and devices for spinal stabilization and fusion, and particularly to stabilization and fusion of a facet joint.

BACKGROUND

The vertebrae in a patient's spinal column are linked to one another by the intevertebral disc and the facet joints. This three joint complex controls the movement of the vertebrae relative to one another. Each vertebra has a pair of articulating surfaces located on the left side, and a pair of articulating surfaces located on the right side, and each pair includes a superior articular surface and an inferior articular surface. Together the superior and inferior articular surfaces of adjacent vertebrae form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. In the lumbar spine, for example, one form of treatment to stabilize the spine and to relieve pain involves fusion of the facet joint. There are various techniques for stabilizing and treating the facet joint. However, current instrumentation can limit the available techniques by requiring specific insertion trajectories and/or by providing limited options for securement to the various anatomies surrounding the facet joint.

Accordingly, there is a need for instrumentation and techniques that can facilitate insertion and securement of implants in various orientations and to varied bony anatomies to facilitate the safe and effective stabilization of facet joints.

SUMMARY

Spinal implants and methods relating to stabilization and/or fusion of a facet joint. In general, the implant functions as a sort of mechanical staple and/or key that prevents sliding motion between the diarthroidal surfaces of the facet joint. Further, the spinal implant can include a fusion-promoting bioactive material thereby providing for a single spinal implant capable of allowing for both fixation and fusion of a desired facet joint. Various aspects of the implants and methods are summarized immediately below.

In one aspect, the spinal implant can include a cannulated elongate member having a proximal head with a shank extending distally therefrom. The shank can have a thread extending over at least a portion thereof, and a portion thereof can remain unthreaded. In some embodiments, the proximal head can be substantially spherical with an annular rim extending proximally therefrom. The spinal implant can also include a stabilization member configured to rotate in all directions relative to the proximal head of the elongate member. In another embodiment, the stabilization member can have a proximal portion with an expandable diameter that is configured to seat the proximal head of the elongate member. The annular rim can be configured to limit rotation of the stabilization member to prevent the stabilization member from extending over a proximal surface of the proximal head.

The stabilization member can have many configurations and can include a distal portion having at least one feature configured to engage a bony portion of a facet joint. For example, the distal portion can include a plurality of bone piercing tines configured to engage a bony portion of a facet joint. An outer surface of the plurality of bone piercing tines can be angled inward toward the shank. The proximal portion of the stabilization member can include a plurality of arms configured to expand to engage the proximal head.

The proximal head can also have many configurations. For example, the proximal head can include an expandable opening formed in a proximal portion thereof and concentrically aligned with the annular rim. In some embodiments, the expandable opening can be configured to receive a set screw. The proximal head and the annular rim can include at least one slit formed in a sidewall thereof configured to allow the proximal head to expand to receive a set screw. The proximal head and the annular rim can be configured to expand to engage and interlock with the stabilization member when a set screw is disposed within the expandable opening. The proximal head can also include a driving feature disposed distally to the expandable opening and configured to receive a driving tool to facilitate insertion of the elongate member. Any portion of the implant can include a fusion-promoting bioactive material.

In another aspect, a spinal implant is provided and can include a distal bone engaging shank having a thread extending over at least a portion thereof. A head can be formed on a proximal end of the shank and can be coupled to a stabilization member. The head can be configured for rotational movement in all directions relative to the stabilization member, and a rotation stop can be formed on a proximal portion of the head and configured to engage a proximal portion of the stabilization member to limit rotational motion of the head relative to the stabilization member. In some embodiments, the rotation stop can be an annular rim extending proximally from the head. The head can optionally include an expandable opening formed therein configured for receiving a set screw. The head can be configured to expand and interlock with the stabilization member when a set screw is threaded into the expandable opening.

The stabilization member can have many configurations and can include, for example, an annular expandable sidewall configured to receive the head. The sidewall can have a radius greater than a radius of the annular rim, and at least a portion of the annular expandable sidewall can be configured to engage at least a portion of the annular rim to limit rotational motion of the head relative to the stabilization member. The stabilization member can also include a plurality of bone engaging tines extending distally from the annular expandable sidewall and configured to engage bone. The stabilization member can have a length and a width orthogonal to the length, the length being greater than the width. In one embodiment, the stabilization member can include a plurality of expandable arms extending proximally therefrom in a substantially circular configuration. The expandable arms can be configured to receive the head and a central axis of the expandable arms can be offset from a central axis of the stabilization member. In some embodiments, the stabilization member can include a bend zone formed therein configured to allow one side of the stabilization member to bend relative to an opposite side of the stabilization member to conform to a bone surface. The stabilization member can also include a cavity formed therein configured to be filled with a fusion-promoting bioactive material.

In a further aspect, a spinal implant is provided and can include an elongate member having a distal shank with a thread extending over at least a portion thereof and a substantially spherical proximal head coupled to a stabilization member. The stabilization member can be configured to allow rotation of the elongate member in all directions relative to the stabilization member. In some embodiments, the stabilization member can include a plurality of expandable arms defining an opening for receiving the proximal head, and can be movable between a first diameter which is less than a diameter of the proximal head and a second diameter which is greater than the diameter of the proximal head.

In one embodiment, the proximal head can include an annular rim extending proximally therefrom and configured to engage the plurality of expandable arms to limit rotation of the elongate member. The stabilization member can also include a plurality of bone engaging tines extending distally therefrom. The proximal head can optionally be expandable, and the plurality of expandable arms can be disposed in a substantially circular configuration defining a central axis. In another embodiment, the stabilization member can include a lateral extension such that the central axis of the expandable arms are offset from a central axis of the stabilization member. The stabilization member can further include a bend zone disposed between the lateral extension and the expandable arms. The bend zone can be configured to allow the lateral extension to be bent at an angle relative to the expandable arms.

In another aspect, a spinal implant is provided and can include a cannulated elongate member having a first bone engaging portion with a first diameter and a second bone engaging portion with a second diameter. While the first and second bone engaging portions can have any diameter, in some embodiments, the first diameter can be greater than the second diameter. The first bone engaging portion can be configured for insertion into a facet joint and the second bone engaging portion can be configured for insertion into a pedicle. In some embodiments, at least one of the first and second bone engaging portions can have at least one opening formed in a sidewall thereof and configured to receive an osteoconductive composition.

The spinal implant can include a stabilization member configured to seat the elongate member. The stabilization member can have a first expandable portion configured to engage a portion of the elongate member and a second bone engaging portion having a plurality of bone engaging tines extending therefrom. Each bone engaging tine can be angled toward a central axis of the elongate member. In one embodiment, at least one of the first and second bone engaging portions can have a plurality of openings formed in the sidewall thereof. Each of the plurality of openings can be a different shape.

The elongate member can include a proximal head with a shank extending distally therefrom. The shank can have a thread extending over at least a portion thereof. The first expandable portion of the stabilization member can include a plurality of substantially flexible arms arranged in a circular configuration. Each arm can be separated from adjacent arms by a slit configured to allow expansion and contraction of the arms. In some embodiments, the plurality of substantially flexible arms are configured to receive a proximal head of the elongate member and to allow rotation in all directions of the proximal head relative thereto. The stabilization member can optionally include a lateral extension such that a central axis of the first expandable portion is offset from a central axis of the stabilization member. The lateral extension can be configured to bend relative to the first expandable portion to conform to a bony surface adjacent to a facet joint as the elongate member is positioned within the facet joint.

In a further aspect, a spinal implant is provided and can include an elongate member having a proximal head and a bone engaging shank extending distally from the proximal head. The proximal head can be configured for rotational movement in all directions within a stabilization member. In some embodiments, the shank can have at least first and second openings formed in a sidewall thereof and can be configured to receive an osteoconductive composition. The shank can further have a thread extending over at least a portion thereof, and a first portion with a first major diameter and a second portion with a second major diameter, in which the first major diameter can be greater than the second major diameter.

In one embodiment, the first and second openings can be disposed along a longitudinal axis of the elongate member. The first and second openings can have many different configurations including different sizes and different shapes. The spinal implant can also include a stabilization member configured to seat the elongate member. In some embodiments, the stabilization member can include a stabilizing plate portion having a plurality of bone engaging tines extending distally therefrom for piercing bone. Further, the stabilization member can include a stabilizing plate portion having a plurality of expandable arms extending proximally therefrom configured to receive the proximal head of the elongate member.

While the stabilizing plate portion can have many configurations, in one embodiment, the stabilizing plate portion can have a length extending between first and second opposed sides and a width extending between third and fourth opposed sides, wherein the length is greater than the width. The stabilizing plate portion can optionally include an extension member extending distally from one of the first and second opposed sides. The extension member can have a length greater than a length of the plurality of bone engaging tines. In another embodiment, the stabilizing plate portion can include at least one bendable region disposed thereon such that the stabilizing plate portion is bendable along a line orthogonal to the length of the stabilizing plate portion.

In one exemplary embodiment, the stabilization member can include a translation plate disposed adjacent to the stabilizing plate portion. The translation plate can have a plurality of expandable arms extending proximally therefrom configured to receive the proximal head of the elongate member and to allow rotational movement of the proximal head in all directions relative to the stabilization member. The translation plate can be configured to translate laterally with the elongate member relative to the stabilizing plate portion along the length of the stabilizing plate portion.

In other embodiments, the stabilizing plate portion can include a plurality of expandable arms extending proximally therefrom defining a first opening disposed adjacent to one of the first side and the second side and offset from a central axis of the stabilizing plate portion, as well as a second opening formed on the first or second side opposite to that of the first opening. The expandable arms can be configured to receive the proximal head, and the first opening can be configured to receive the elongate member. The second opening can be configured to receive the second elongate member therethrough. In some embodiments, the second elongate member can be a lamina screw configured to engage a lamina while the elongate member is engaged within a facet joint. The stabilizing plate portion can also optionally include a first portion and a second portion, the first and second portions being coupled together by an adjustable coupling. The adjustable coupling can be configured to allow translation of the first portion relative to the second portion and bending of the first portion relative to the second portion.

In another aspect, a method of implanting a spinal implant is provided and can include providing an elongate member having a first bone engaging portion and a second bone engaging portion. At least one of the first and second bone engaging portions can have at least one opening formed therein for receiving an osteoconductive composition. The method can further include packing an osteoconductive composition into the opening and surgically delivering the elongate member into a vertebra such that the first bone engaging portion is disposed within a facet joint and the second bone engaging portion is disposed within a pedicle. The method can also include engaging a stabilization member coupled to the elongate member to a bony portion of a vertebra adjacent to the facet joint in which the elongate member is disposed. Further, the stabilization member can be bent to engage a bony portion of a vertebra adjacent to the facet joint in which the elongate member is disposed.

In some embodiments, the method can further include delivering a first spinal implant to a first facet joint and a second spinal implant to a second, corresponding facet joint at the same level of a spine. The surgically delivering step can be conducted in a minimally invasive surgical procedure. A lamina screw can also be delivered to a vertebral lamina through an opening in the stabilization member to provide additional stabilization for the elongate member disposed within the facet joint.

These aspects and others will be described in detail below.

BRIEF DESCRIPTION OF THE DRAWINGS

The invention will be more fully understood from the following detailed description taken in conjunction with the accompanying drawings, in which:

FIG. 2A is a perspective view of an exemplary spinal implant having an elongate member and a stabilization member;

FIG. 2B is a side view of a portion of the implant of FIG. 2A;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Figure 1A:
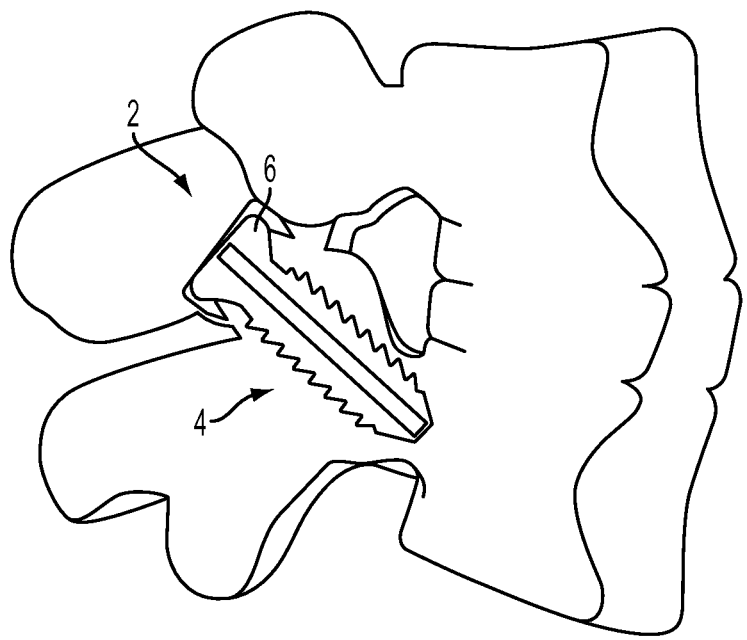
FIG. 1A is a cross-sectional view of an exemplary implant disposed within a facet joint.
Figure 1B:
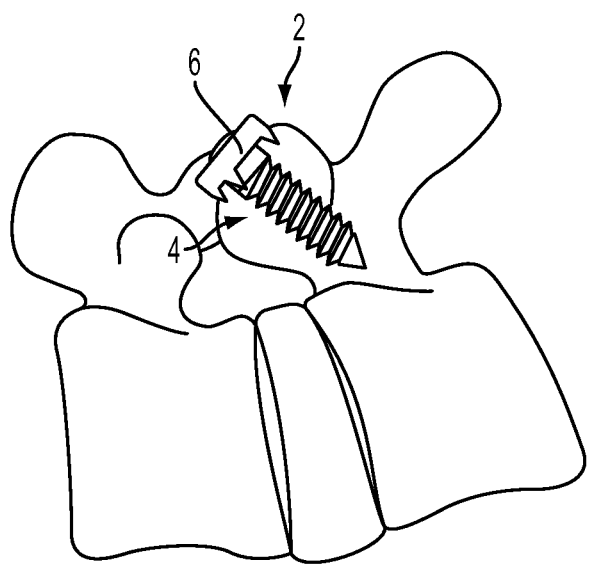
FIG. 1B is a perspective view of the spinal implant of FIG. 1A.

In general, spinal implants and methods for spinal stabilization and/or fusion are provided. Exemplary implants described herein can be configured for delivery to a facet joint to stabilize and/or fuse the facet joint, and can optionally be anchored within the pedicle for added fixation. As shown in FIGS. 1A and 1B, an exemplary implant 2 can generally include an elongate member 4, such as a bone screw or fastener, polyaxially coupled to a stabilization member 6, such as a bone engaging washer. The elongate member 4 can be disposed within the facet joint as shown, while the stabilization member 6 can engage an outer portion (e.g., an edge) of a facet joint to co-join the facet faces. In an exemplary method of using the implant 2, the elongate member 4 and the stabilization member 6 can be delivered to and inserted within and/or around the facet joint in a desired configuration and at a desired angle. The stabilization member 6 and the elongate member 4 can be rotated polyaxially (e.g., in all directions) relative to one another to achieve an optimal angle within and/or around the facet joint before being secured thereto. For example, the relative angular orientation of the elongate member 4 and the stabilization member 6 can thus be adjusted as needed to accommodate different positions within the facet joint, as well as various shaped anatomical structures, thereby allowing for a better fit of the implant 2.

Any of the exemplary implants described herein can also have features that allow for variable placement of a stabilization member and/or an elongate member within and/or around the facet joint to facilitate facet stabilization and/or fusion. For example, exemplary stabilization members can have laterally extended portions and/or bendable portions that allow for the placement of additional securement components, and that generally allow for more flexibility in placement of the implant in and around the facet joint. In addition, exemplary implants can have repositioning mechanisms and/or adjustable couplings associated therewith that allow variability in the anchoring trajectory of the implant. Various exemplary embodiments of elongate members and stabilization members for use in these ways will be described herein.

Referring now to FIGS. 2A and 2B, a more detailed exemplary embodiment of a spinal implant 10 is provided. The spinal implant 10 can include an elongate member 14 coupled to a stabilization member 12. The elongate member 14 can extend from a distal end 16 to a proximal end 18. A head 20 can be formed on the proximal end 18, and a shank 22 can extend distally from the head 20. The stabilization member 12 can couple to the head 20 of the elongate member 14 by circumferentially encircling the head 20. The elongate member 14 can generally be configured to rotate polyaxially relative to the stabilization member to allow the stabilization member 12 to adapt to various anatomical structures during placement within the facet joint.

The elongate member 14 can take many different forms, including the forms of a pin, a dowel, a plug, a beam, a post, a threaded post, a bolt, an expansion barrel, a pop-rivet, a staple, an anchor, a screw, etc. In the illustrated embodiment, the elongate member 14 is in the form of a bone screw configured for placement within a facet joint. The elongate member 14 can be cannulated such that a lumen 15 extends through the elongate member 14 along a central longitudinal axis of the elongate member 14. The lumen 15 can be configured to receive a guide wire, such as a Kirschner wire, to help facilitate insertion of the implant 10 and/or can be configured for packing with a bioactive osteoconductive composition, as will be described in more detail below. In other embodiments, the elongate member 14 can be solid, without a lumen 15 extending therethrough.

The elongate member 14 can also include one or more features to facilitate engagement between the shank 22 and bone. For example, a thread 24 can extend around at least a portion of the shank 22 of the elongate member 14 to facilitate engagement between the shank 22 and bone. In some embodiments, at least a portion 25 of the shank 22 can remain unthreaded. As will be appreciated by those skilled in the art, any portion of the shank 22 can be threaded or unthreaded. For example, all of the shank 22 can be threaded or all of the shank 22 can remain unthreaded, and the thread 22 can be continuous or non-continuous. Further, the shank 22 can include more than one thread, including two helical threads and/or two or more threads having different pitches, different major diameters, etc. The shank 22 can have a major diameter $D_M$ defined by the outer diameter of the threads, and a minor diameter $D_m$ defined by the diameter of the unthreaded shank. In the illustrated embodiment, the thread 22 can have a substantially constant thread crest height, thickness, and pitch along a length of the shank 22. As will be appreciated by those skilled in the art, thread parameters can be optimized for a particular embodiment to provide desired engagement characteristics in the bone.

The head 20 of the elongate member 14 can also have many configurations, and can have any size and shape as desired. In the illustrated embodiment, the head 20 is substantially spherical with a diameter larger than the major diameter $D_M$ of the shank 22. The head 20 can also be substantially cylindrical, rectangular, etc. and can have a diameter smaller than a diameter $D_M$ of the shank. The head 20 can have an opening 26 formed in a proximal end thereof that can be configured for receiving a driving tool to facilitate insertion of the elongate member 14. For example, the opening 26 can have features formed therein that will complement features on a driving tool to facilitate rotation of the elongate member 14 into bone. The head 20 can also include an annular rim 28 extending proximally therefrom. In the illustrated embodiment, a circumference of the annular rim 28 defines the opening 26. The annular rim 28 can have any height and width desired, and can have a circumference and/or diameter as is appropriate for a particularly sized head 20. For example, the annular rim can have a diameter in the range of about 3 mm to about 10 mm and a height in the range of about 0.25 mm to about 5 mm. In some embodiments, the height of the annular rim 28 can be sufficient to limit rotation of the elongate member 14 relative to the stabilization member 12 by preventing the stabilization member 12 from rotating over the proximal end 18 of the elongate member 14, as will be described in more detail below.

The stabilization member 12 can generally be configured to stabilize the elongate member 14 when it is engaged with bone and to prevent over-insertion of the elongate member 14. As shown in FIGS. 2B and 3B, the stabilization member 12 can have a substantially circular and/or partial spherical shape for encircling the substantially spherical head 20 of the elongate member 14. The stabilization member 12 can include a stabilizing plate portion portion 30 having an elongate member receiving portion 34 extending proximally therefrom for receiving the head 20 of the elongate member 14, and a bone engaging portion 36 extending distally therefrom for engaging bone. The stabilizing plate portion 30 can be a plate-like member, which may or may not be continuous, and that extends in a lateral plane orthogonal to a central axis CA of the stabilization member 12. An opening 32 can extend through a center of the stabilization member 12 and can be concentrically aligned with a central axis CA of the stabilization member 12.

The elongate member receiving portion 34 extending proximally from the stabilization member 12 can have any configuration suitable for receiving the head 20 of the elongate member 14. In the illustrated embodiment, the elongate member receiving portion 34 can have a partial spherical shape so that it can receive the substantially spherical head 20 of the elongate member 14. More particularly, the elongate member receiving portion 34 can be composed of one or more flexible and/or expandable arms 38 that extend proximally from the stabilizing plate portion 30. In the illustrated embodiment, a plurality of the flexible and/or expandable arms 38 extend proximally from the stabilizing plate portion 30 and are each separated by a slit or opening 40 to allow expansion and contraction thereof. The arms 38 can provide the stabilization member 12 with a "snap-fit" onto the spherical head 20 and can allow polyaxial movement of the stabilization member 12 relative to the head 20. The arms 38 can have any shape and configuration desired, but in the illustrated embodiment, each arm 38 has a substantially rounded wedge shape such that an inner surface 56 of the arm 38 is curved to match the curve of the substantially spherical head 20 of the elongate member 14. An outer surface 58 of the arm 38 can curve distally outward in a wedge configuration. A distal portion of each arm 38 can be thinned to form a bend zone 58 to provide the arms 38 with flexibility such that the arms 38 flex, expand, and contract, about the bend zone 58.

As noted above, the stabilization member 12 can also have a bone engaging portion 36 extending therefrom. The bone engaging portion 36 of the stabilization member 12 can have any configuration suitable for engaging, gripping, piercing, and/or penetrating bone. One or more features can extend distally from the stabilizing plate portion 30 to facilitate engagement with the bone. In the illustrated embodiment, a plurality of bone engaging tines 42 extend distally from the stabilizing plate portion 30 and can be configured for engaging, gripping, piercing, and/or penetrating bone. The tines 42 can be of different sizes and shapes, and can be adapted to perform different functions as needed. In this embodiment, the tines 42 can decrease in width as they extend distally until they form a bone piercing and/or penetrating tip 44.

The tines 42 extending from the stabilizing plate portion 30 can be arranged in many configurations. In some embodiments, a proximal portion 46 of the tine 42 can extend distally and substantially orthogonally from the stabilizing plate portion 30 such that the tines 42 have an outer diameter substantially the same as an outer diameter of the stabilizing plate portion 30. An outer surface 48 of a distal portion 54 of the tine 42 can bend inward toward the shank 22 such that the outer surface 48 of the distal portion 54 is angled relative to the outer surface 50 of the proximal portion 46, for example at an angle in a range of about 5 degrees to about 60 degrees, and more preferably in a range of about 10 degrees to about 45 degrees. An inner surface 52 of the tine 42 can remain at a substantially constant angle (i.e., substantially orthogonal to the stabilizing plate portion 30) or it can curve inward slightly toward the shank 22 with a radius of curvature in the range of about 5 mm to about 20 mm, for example about 13 mm, as it extends distally from the stabilizing plate portion 30 across the proximal portion 54 and the distal portion 46.

The structure of the tines 42 provide easier bone penetration and a more secure engagement between the bone and the stabilization member. In particular, as the bone engaging tines 42 are driven into bone, the angled outer surface 50 of the tines 42 will cause the stabilization member 12 to close down and inward to provide a more secure purchase within bone. In use, when the elongate member 14 is disposed within a facet joint, a first tine 42 and/or first set of tines 42 can pierce a top vertebra (or top facet face) while a second tine 42 and/or second set of tines 42 can pierce an adjacent, bottom vertebra (or opposing facet face). As such, the stabilization member 12 can effectively act in a staple-like manner securing the implant 10 within the facet joint.

As noted above, the implant 10 can include features to limit rotation of the elongate member 14 relative to the stabilization member 12. For example, as also noted above, the head 20 of the elongate member 14 can include an annular rim 28 extending proximally therefrom that can be configured to limit rotation of the elongate member 14 relative to the stabilization member 12 by preventing the stabilization member 12 from rotating over the proximal end 18 of the elongate member 14. When the stabilization member 12 is coupled to the head 20 of the elongate member 14, it can rotate polyaxially (i.e., in all directions) relative to the elongate member 14 due to the complementary spherical shape between the head 20 of the elongate member 14 and the elongate member receiving portion 34 of the stabilization member 12. The annular rim 28, however, can limit the rotation of the stabilization member 12 by blocking the arms 38 from rotating further over the top of the head 20 of the elongate member 14. More particularly, as the stabilization member 12 rotates relative to the head 20, the arms 38 can engage the annular rim 28, which can prevent the stabilization member 12 from rotating further in that direction. The stabilization member 12 can rotate in all directions relative to the elongate member 14 such that the central axis CA of the stabilization member 12 is at an angle α relative to a central longitudinal axis LA of the elongate member 14 in the range of about 0 degrees to about 30 degrees. In other words, when the arms 38 of the stabilization member 12 are engaged with the annular rim 28, the central axis CA of the stabilization member 12 can be at an angle of about 30 degrees relative to the longitudinal axis LA of the elongate member 14.

Figure 3A:
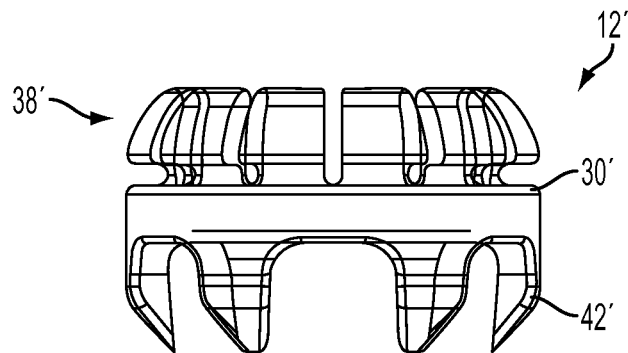
FIG. 3A is a side view of one embodiment of a stabilization member.
Figure 3B:
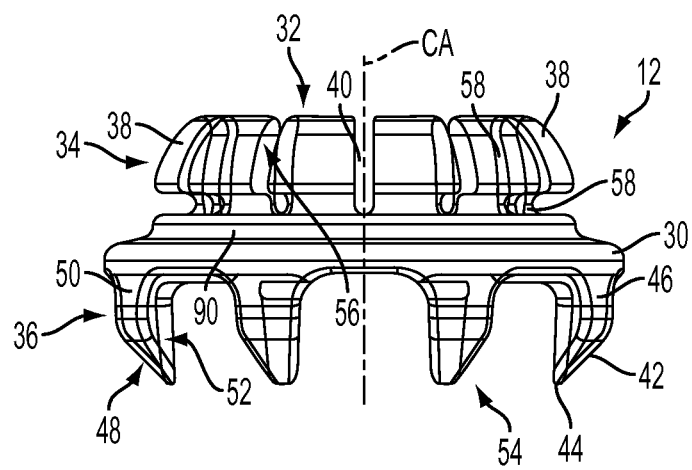
FIG. 3B is a side view of the stabilization member of FIG. 1A.
Figure 3C:
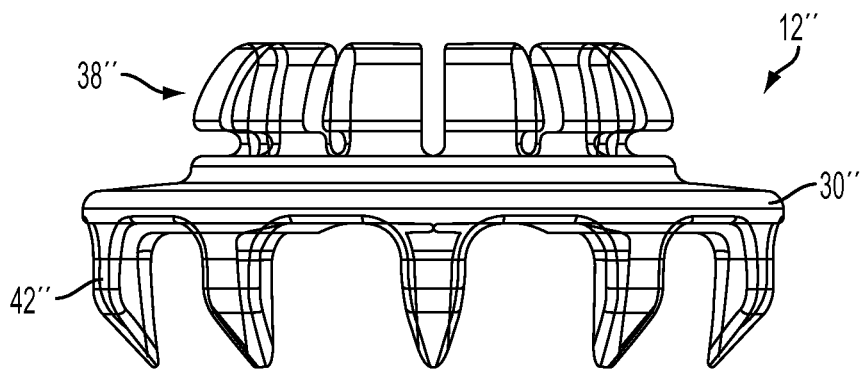
FIG. 3C is side view of another embodiment of a stabilization member.

Other exemplary stabilization members are illustrated in FIGS. 3A and 3C. As shown, stabilization members 12', 12" are provided and can have a plurality of expandable arms 38', 38" extending proximally from a stabilizing plate portion 30', 30" and a plurality of bone engaging tines 42', 42" extending distally from the stabilizing plate portion 30', 30". In the embodiment of FIG. 3A, the stabilizing plate portion 30' has an outer diameter substantially the same as an outer diameter of the expandable arms 38'. The outer diameter can be in the range of about 8 mm to about 20 mm, and more preferably in the range of about 10 mm to about 15 mm, for example, about 13 mm. As shown in FIG. 3B, the stabilizing plate portion 30 can have an outer diameter larger than an outer diameter of the expandable arms 38. The outer diameter of the stabilizing plate portion 30 can be in the range of about 10 mm to about 25 mm, and more preferably in the range of about 13 mm to about 20 mm, for example about 16 mm. The stabilizing plate portion shown in FIG. 3C can have an outer diameter substantially larger than an outer diameter of the expandable arms 38". The outer diameter of the stabilizing plate portion 30" can be in the range of about 13 mm to about 30 mm, and more preferably in the range of about 15 mm to about 25 mm, for example about 19 mm. As will be appreciated by those having ordinary skill in the art, the stabilizing plate portions 30, 30', 30" and the expandable arms 38, 38', 38" can have any diameter as desired relative to one another and relative to an elongate member utilized therewith. The various exemplary stabilization members 12, 12', 12" can also have any height as desired. For example, a particular stabilization member 12, 12', 12" can have a height in the range of about 1 mm to about 15 mm, and more preferably between about 5 mm to about 10 mm, for example, about 6 mm, 7 mm, 8 mm, 9 mm, etc. As will be appreciated by those having ordinary skill in the art, the stabilization members 12, 12', 12" can be used with any of the various elongate members described herein.

Figure 4A:
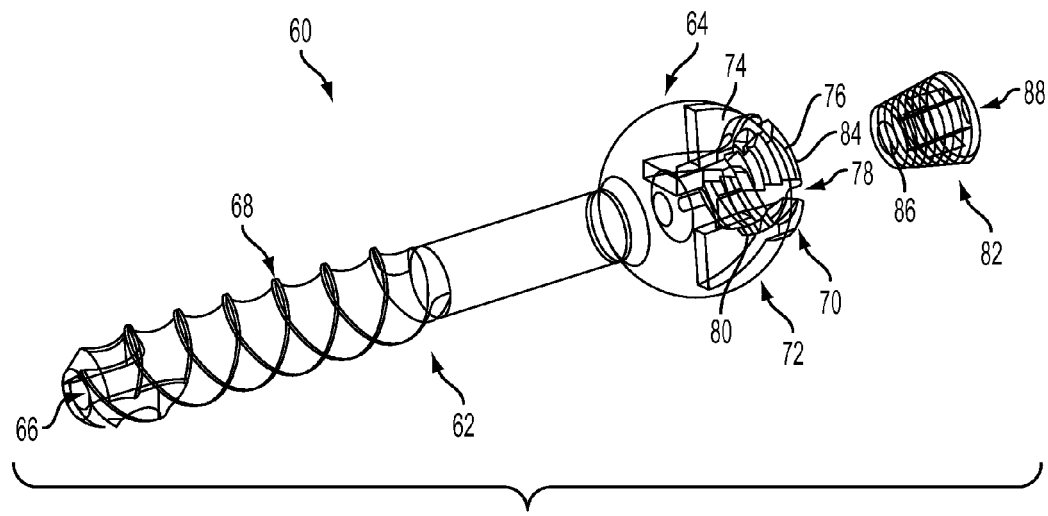
FIG. 4A is a perspective view of one embodiment of a spinal implant having an expandable head.
Figure 4B:
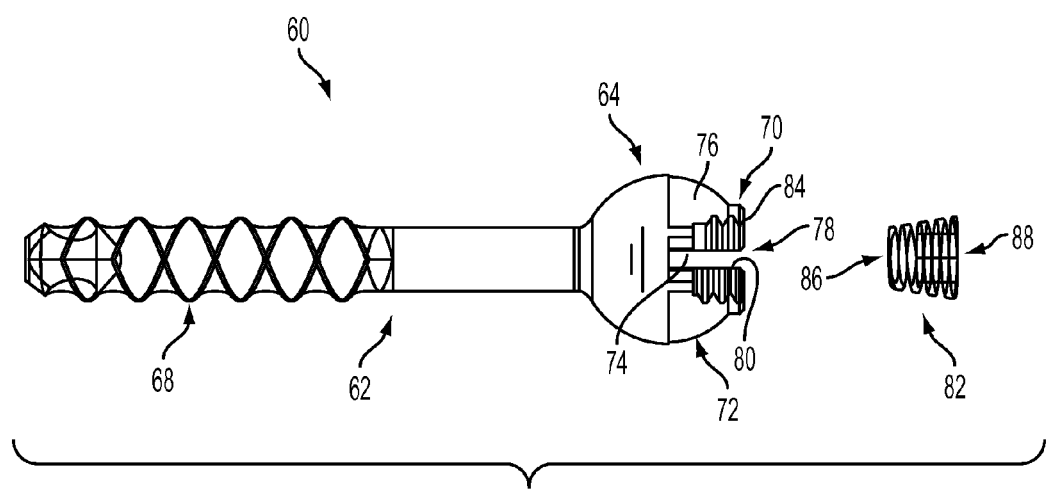
FIG. 4B is a side view of an exemplary elongate member having openings formed therein for receiving a bio-active fusion promoting composition.

Another embodiment of an elongate member 60 is illustrated in FIGS. 4A and 4B. Similar to the elongate member 14 above, the elongate member 60 can have a shank 62 extending distally from a substantially spherical head 64. The elongate member 60 can be cannulated with a lumen 66 extending longitudinally therethrough, and the shank 62 can include a thread 68 extending over at least a portion thereof. Further, the head 64 can include an annular rim 70 extending proximally therefrom for limiting rotation of a stabilization member (not shown). A proximal portion 72 of the head 64 can optionally include one or more slots 74 formed therein to allow the head 64 to be expandable. In the illustrated embodiment, the head 64 includes four slots 74 formed through a sidewall of the head 64 and through the annular rim 70. The four slots 74 define four arms 76 in the proximal portion 72 of the head 64 that can expand and contract around an opening 78 formed in the head 64.

While the opening 78 in the head 64 can have many configurations, in the illustrated embodiment, a distal portion of the opening 78 can be configured to receive a delivery tool to facilitate insertion of the elongate member 60 into bone. A proximal portion of the opening 78 can have a thread 80 extending therearound such that the opening 78 is configured to receive a set screw 82 therein. The set screw 82 can be a threaded member that increases in diameter in a distal to proximal direction such that as the set screw 82 is threaded into the opening 78, it expands the opening 78 due to its increasing width. When the elongate member 60 is coupled to any of the stabilization members described herein, threading the set screw 82 into the opening 78 in the head 64 can cause the head 64 to expand and engage the stabilization member more securely. The set screw 82 can sit flush with a top surface 84 of the annular rim 70 or it can sit a distance below the top surface 84 of the annular rim 70. The set screw 82 can be cannulated with a lumen 86 that can align with the lumen 66 in the elongate member 60. The set screw 82 can also have an opening 88 formed in a proximal surface thereof for receiving a tool to facilitate insertion of the set screw 82 into the opening 78 in the head 64.

Any of the stabilization members and elongate members described herein can include a bioactive fusion-promoting material capable of actively participating in spinal fusion. The fusion-promoting material can be a surface morphology change, such as a roughened surface, to allow for bony ongrowth, or materials, such as titanium beads or meshes, can be added to allow bony in-growth. In some embodiments, the stabilization member and/or the elongate member can be formed from a bioactive material, thereby allowing the implant to participate in spinal fusion. In other embodiments, the stabilization member or the elongate member can include a portion (or a coating) formed from a bio-active fusion promoting material. In addition, in any of the stabilization member embodiments described herein, a cavity or opening formed within the stabilization member can be filled and/or packed with a bio-active fusion promoting material. The stabilization member shown in FIG. 3B can include a cavity 90 formed therein in which a bio-active fusion promoting material can be packed. In other embodiments, an opening or cavity can be formed within an elongate member for the same purpose. For example, FIGS. 5A-6C and 7 illustrate various embodiments of fusion-promoting elongate members, as will be described below.

The fusion-promoting bioactive material can include any material capable of actively participating in spinal fusion. In an exemplary embodiment, the bioactive material can be allograft bone material (such as Allowashed™ available from LifeNet, Inc.; Virginia Beach, Va.). In another example, the material can be a bioresorbable plastic (poly-lactic acid, polyglycolic acid, their derivatives and/or blends), poly-anhydride (PolymerDrug™ by PolyMerix, Piscataway, N.J.), polymerized sugars or starches (Eureka™ by Surmodics of Eden Prairie, Minn.), bioceramic (HIP Vitox™ alumina or Zyranox™ zirconia by Morgan Advanced Ceramics of Fairfield, N.J.; crystalline hydroxyapatite, tricalcium phosphates or combinations of these materials by Berkeley Advanced Biomaterials of San Leandro, Calif.), bioceramic-loaded bioabsorbable material, or dense protein (Novasilk™ by Protein Polymer Technologies of San Diego, Calif.). Exemplary embodiments of such bioabsorbable materials include Biocryl™ (an 85% PLA/PGA, 15% tricalcium phosphate material available from Depuy Mitek, a Johnson & Johnson Company; Raynham, Mass.) or TriABSorb™ (a 5% hydroxyapatite, 95% PLA material available from Depuy Mitek, a Johnson & Johnson Company; Raynham, Mass.). Preformed plugs produced from TCP or HA. As another example, the material can be an osseointegrating porous polymer such as PEEK/Optima™ (available from Invibio, Inc.; Greenville, S.C.). The bioactive fusion promoting material can be autologus bone graft intra-operatively harvested from the patient. Those skilled in the art will appreciate that any combination of these materials are within the spirit and scope of the present invention.

Figure 5:
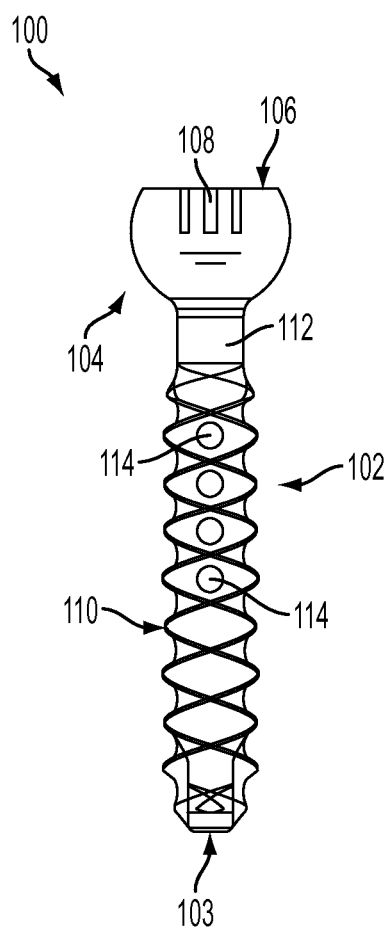
FIG. 5 is a side view of an exemplary elongate member having openings formed therein for receiving a bio-active fusion promoting composition.

In one embodiment shown in FIG. 5, an elongate member 100 is provided having a shank 102 extending distally from a head 104. The elongate member 100 can be cannulated with a lumen 103 and can be configured for being inserted into bone. The head 104 can have any shape and configuration, but in the illustrated embodiment, the head 104 has a substantially spherical body with a flattened proximal top surface 106. An opening 108 can be formed in the head 104 to receive a driving tool to facilitate insertion of the elongate member 100 into bone. The shank 102 can have at least one thread 110 extending therearound, and at least a portion 112 of the shank 102 can remain unthreaded. A major diameter of the head 104 can be greater than a major diameter of the shank 102.

In some embodiments, the shank 102 can optionally include features to promote fusion. For example, the shank 102 can include a plurality of openings 114 formed through a sidewall thereof. While the openings 114 can be any size and shape, in the illustrated embodiment there are four circular openings 114 that extend laterally through the shank 102 in a direction orthogonal to a central longitudinal axis of the elongate member 100. The openings 114 can have a diameter less than a distance between two windings of the thread 110 so that each opening 114 can be positioned between two windings. The openings 114 can be filled and/or packed with a bio-active fusion promoting material that can encourage bone growth through the openings, thereby promoting fusion. The openings 114 can be packed with the bio-active fusion promoting material through the lumen 103 and/or can be packed directly through the openings 114. In some embodiments, the openings 114 can be formed within a proximal portion of the shank 102 that is disposed within the facet joint, as opposed to a distal portion of the shank 102 disposed within a pedicle. In this way, fusion between the facet faces is promoted through the use of the openings 114 filled with the bio-active composition.

Figure 6A:
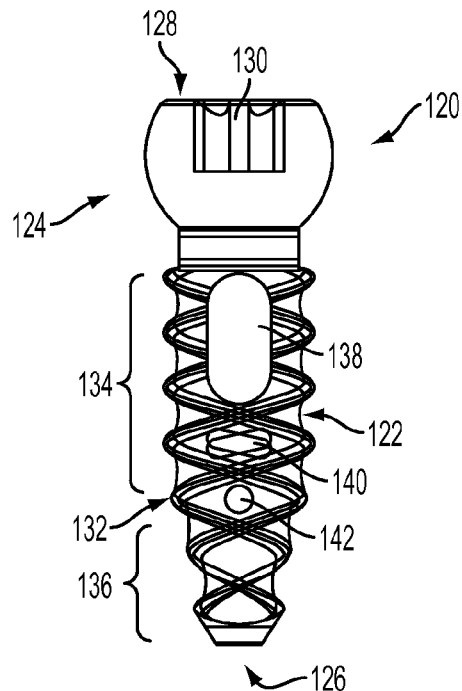
FIG. 6A is a side view of an exemplary elongate member having a shank with two different major diameters.
Figure 6B:
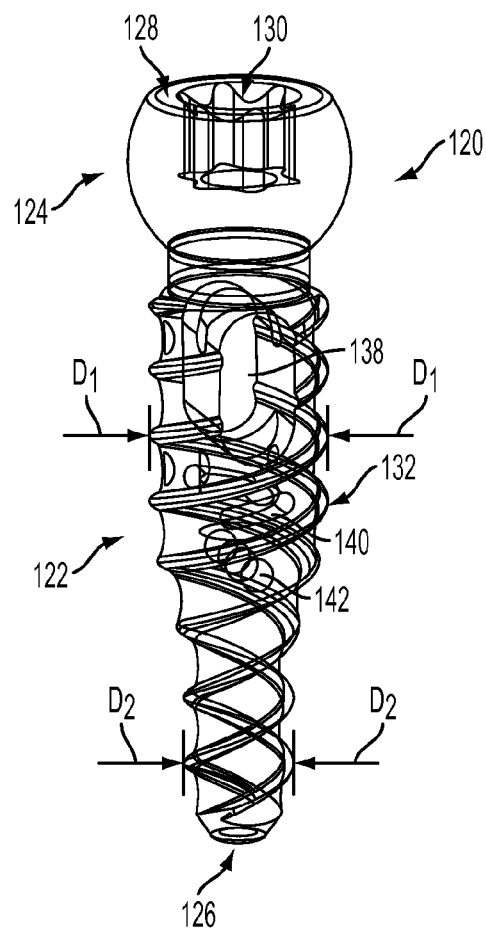
FIG. 6B is a perspective view of the elongate member of FIG. 6A.

Another exemplary elongate member 120 is illustrated in FIGS. 6A and 6B. As shown, the elongate member 120 can include a shank 122 extending distally from a head 124. The elongate member 120 can be cannulated with a lumen 126 extending therethrough and can be configured to be inserted into bone. The head 124 can have any shape and configuration, but in the illustrated embodiment, the head 124 has a substantially spherical body with a flattened proximal top 128. An opening 130 can be formed in the head 124 to receive a driving tool to facilitate insertion of the elongate member 120 into bone. The shank 122 can have at least one thread 132 extending therearound. In the illustrated embodiment, the shank 122 can have two portions with different diameters. A proximal portion 134 of the shank 122 can have a first major diameter $D_1$, and a distal portion 136 of the shank 122 can have a second major diameter $D_2$. In this case, the first major diameter $D_1$ is greater than the second major diameter $D_2$ such that the larger first diameter $D_1$ can be positioned between and/or within the facet joint faces, enabling the elongate member 120 to be stronger at this superficial location. In addition, the larger diameter $D_1$ can better enable joint stabilization by acting as a "key" to prevent facet face sliding motion. Furthermore, in some embodiments, the proximal portion 134 with the larger diameter $D_1$ can have material removed from sidewalls thereof to enable a bone graft cage configuration that will encourage bone growth through the elongate member 120 that spans the facet faces and provides further mechanical stabilization of the facet joint. A major diameter of the head 124 can be greater than the first and second major diameters $D_1$, $D_2$ of the shank, although as will be appreciated by those having ordinary skill in the art, the major diameter of the head 124 can also be substantially the same as or smaller than the first major diameter $D_1$ or the second major diameter $D_2$.

The shank illustrated in FIGS. 6A and 6B can also have features to promote fusion. As shown, the shank 122 can include various sized and shaped openings formed in a sidewall thereof. The shank 122 can include, for example, three openings spaced longitudinally along a length of the shank 122 that extend laterally through the body of the shank 122. A first opening 138 can be an oblong shaped opening that has a width less than a minor diameter of the shank 122 and a height that spans at least two windings of the thread 132. A second opening 140 can also be an oblong opening positioned distal to the first opening 138, but with a width greater than its height such that it can be positioned between two windings of the thread 132. A third opening 142 can be a circular opening positioned distal to the first and second openings 138, 140 and having a diameter less than the space between two windings of the thread 132. The openings 138, 140, 142 can be filled and/or packed with a bio-active fusion promoting material that can encourage bone growth through the openings 138, 140, 142, thereby promoting fusion.

Figure 12A:
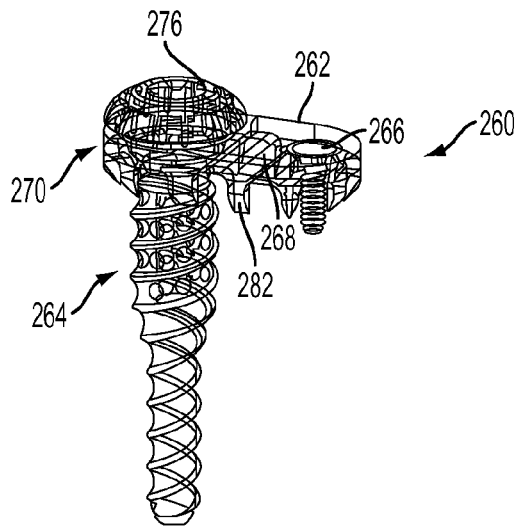
FIG. 12A is a perspective view of an exemplary implant having a laterally extended stabilization member with a lamina screw.
Figure 12B:
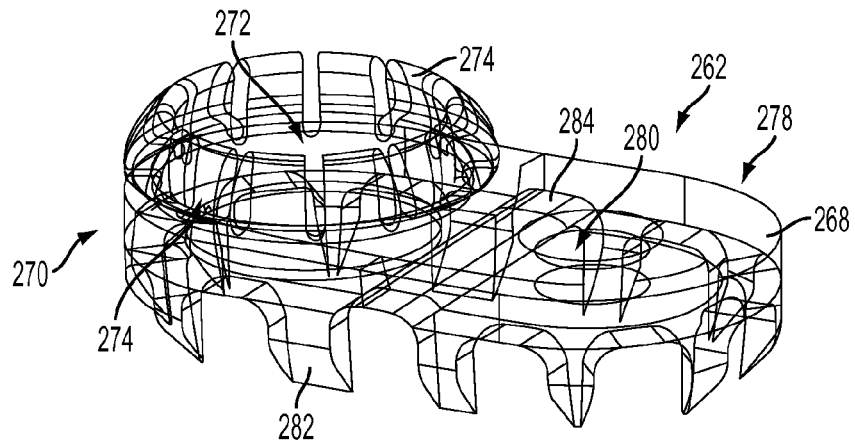
FIG. 12B is an alternate perspective view of the stabilization member of FIG. 12A.
Figure 12C:
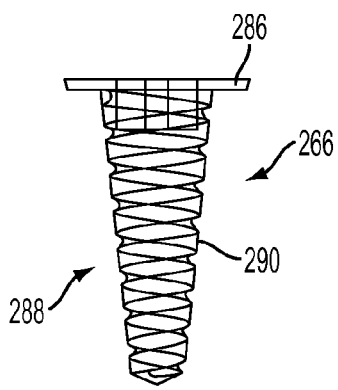
FIG. 12C is a side view of the lamina screw of FIG. 12A.
Figure 12D:
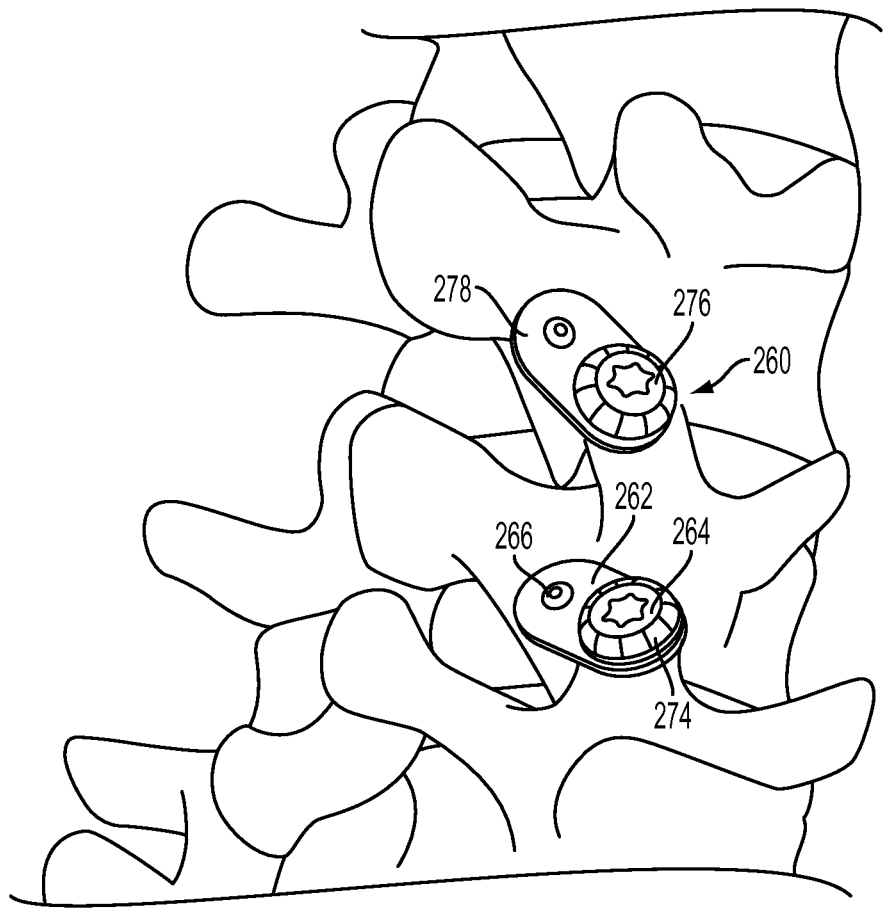
FIG. 12D is a representation of the implant of FIG. 12A positioned within the facet joint.
Figure 12E:
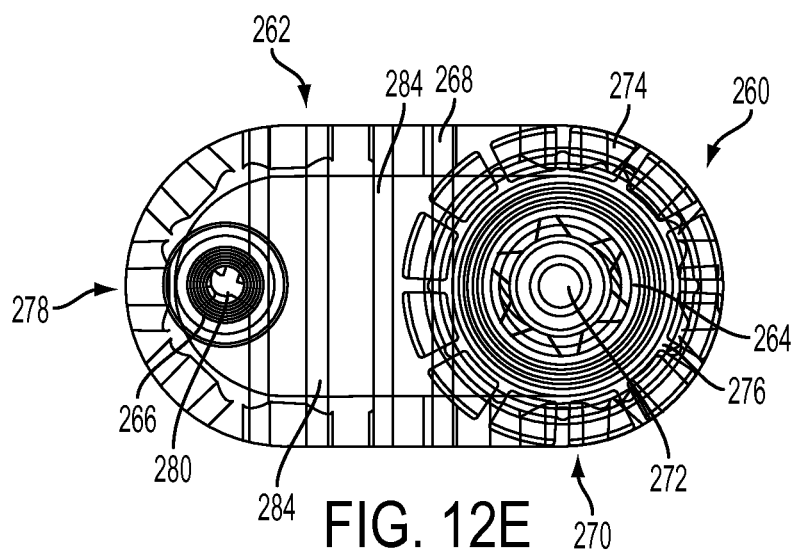
FIG. 12E is a top view of the implant of FIG. 12A.

As will be appreciated by those skilled in the art, any of the elongate members described herein can have any number of openings formed therein, in any configuration. For example, in addition to two opposing openings within a sidewall of a shank (i.e., one opening laterally extending through the shank), there can be any number of openings formed around a circumference of the shank, such as in the elongate member illustrated in FIG. 12A. A plurality of openings can be formed around the circumference of a shank, positioned between windings of the thread, such that there are, for example, 3, 4, 5, 6, 7, 8, 9, 10, or more openings formed around a circumference of the shank. These openings can have any desired shape and size. Further, any number of openings can be positioned longitudinally along a length of the shank of the elongate member.

Figure 7:
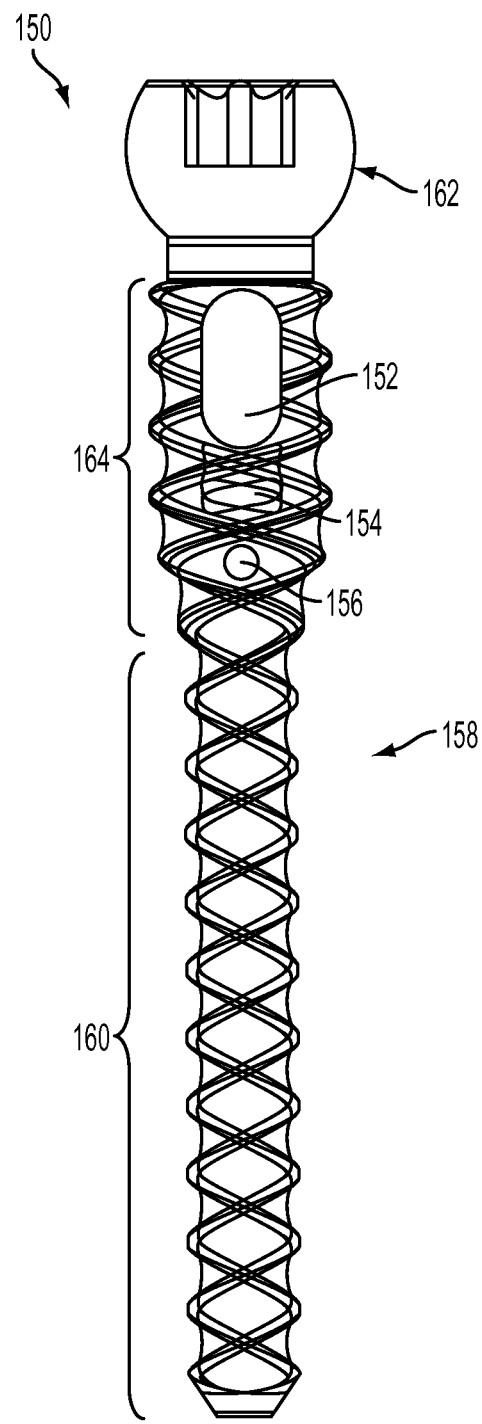
FIG. 7 is a side view of another embodiment of an elongate member having a distal portion for insertion into a pedicle and a proximal portion for insertion into a facet joint.

Another exemplary elongate member 150 is illustrated in FIG. 7, and is similar to that shown in FIGS. 6A and 6B with a shank 158 extending distally from a head 162. Three laterally extending openings 152, 154, 156 can be formed along a length of the shank 158 in a proximal portion 164 thereof for receiving a bio-active fusion promoting material. In this embodiment, however, a distal portion 160 of the shank is substantially longer than the proximal portion 164. When inserted into a facet joint, the distal portion 160 can extend into the pedicle while the proximal portion 164 is engaged with the facet joint. Anchoring within the pedicle in this way provides the elongate member 150 with greater stability within the facet joint.

The elongate members illustrated in FIGS. 1A-7, and any other elongate member embodiments described herein, can have any particular dimension as needed for a particular procedure or anatomy. For example, a particular elongate member can have a length from a proximal end to a distal end in the range of about 20 mm to about 80 mm. Generally, the elongate members shown in FIGS. 1A-6B can have a length in the range of about 25 mm to about 45 mm, and more preferably in the range of about 30 mm to about 40 mm, for example about 30 mm or about 35 mm. Generally, the elongate member shown in FIG. 7 can have a length in the range of about 50 mm to about 70 mm, and more preferably in the range of about 55 mm to about 65 mm, for example 60 mm. A greater diameter of the shanks, including the proximal and the distal portions of a shank that changes diameter, can range from about 2 mm to about 15 mm, more preferably from about 4 mm to about 10 mm, for example, about 5 mm, 6 mm, 7 mm, 8 mm, 9 mm, etc.

Various stabilization members for use with the various elongate members are also provided and can be configured in various alternative shapes and sizes as compared to those substantially circular embodiments discussed above. The stabilization members can be configured to include different types of bone engaging features, including bone engaging tines, serrated/cutting edges, and extension portions, as well as different shaped and sized bone engaging members disposed on one stabilization member. In addition, a particular stabilization member can be configured to include at least one lateral extension that can be in the form of a "plate-like" configuration, resulting in a substantially oblong, rectangular, and/or oval shaped stabilization member. In other embodiments, laterally extended stabilization members can be curvilinear, both laterally and longitudinally. Such embodiments can be utilized in either intra-facet and/or trans-facet stabilization of the facet joint. As will be discussed, a laterally extended configuration allows for broader engagement across the facet joint so that the stabilization member makes contact with bony anatomy adjacent to the facet joint, such as the lamina, lateral facet, or pedicle. This allows the stabilization member to span the facet to secure, stabilize, and fuse the facet faces. In some embodiments, a laterally extended stabilization member can be bendable to provide closer and more complementary engagement across a facet joint.

Figure 8A:
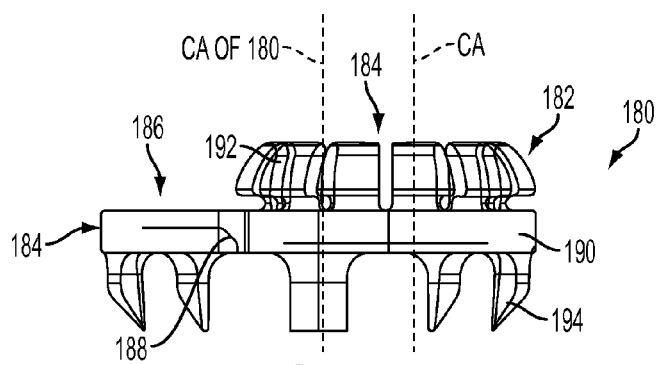
FIG. 8A is a side view of one embodiment of a laterally extended stabilization member.
Figure 8B:
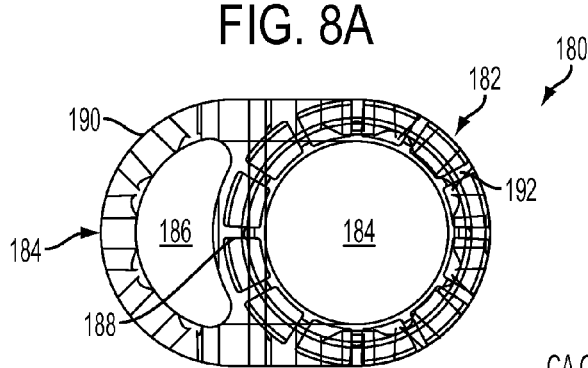
FIG. 8B is a top view of the stabilization member of FIG. 8A.

FIGS. 8A-8B illustrate an embodiment of a stabilization member 180 having an extended lateral profile. The stabilization member 180 can have an elongate member receiving portion 182 with an opening 184 formed therethrough for receiving a head of an elongate member (not shown). The stabilization member 180 can also have an extension portion 184 with an opening 186 formed therethrough. The two portions 184, 186 can be separated by a bend zone region 188 formed in a stabilizing plate portion 190 of the stabilization member 180. The bend zone region 188 can be a thinned portion of the stabilizing plate portion 190 that allows the stabilizing plate portion 190 to be flexible in that region such that the stabilization member 180 can be bent around a facet joint or other boney surface to provide better conformation thereto.

The structure of the stabilization member 180 can be substantially the same as described above relative to the substantially circular stabilization members. A plurality of expandable arms 192 can extend proximally from the stabilizing plate portion 190 in a substantially circular configuration defining the opening 184 through the elongate member receiving portion 182. As shown, a central axis of the opening 184 can be offset from a central axis of the stabilization member 180. The expandable arms 192 can be configured to receive a substantially spherical head of an elongate member.

A plurality of bone engaging tines 194 can extend distally from the oblong shaped stabilizing plate portion 190 around its outer perimeter such that the bone engaging tines 194 are also in an oblong or oval shape. In this way, when the stabilization member 180 is bent along its bend zone region 188, the tines 194 will engage bone around the entire perimeter of the stabilizing plate portion 190.

Figure 9A:
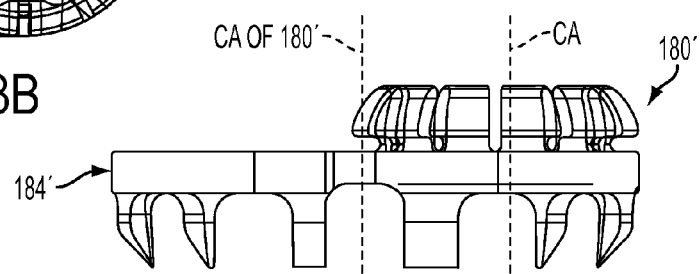
FIG. 9A is a side view of another embodiment of a laterally extended stabilization member.
Figure 9B:
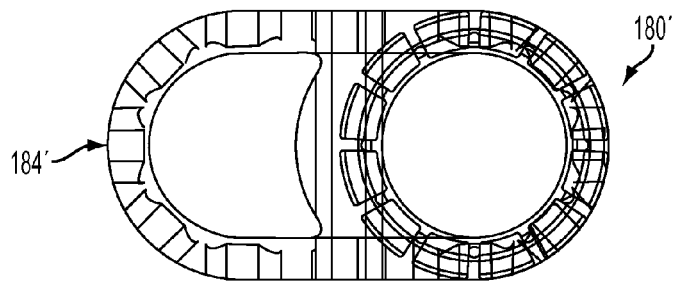
FIG. 9B is a top view of the stabilization member of FIG. 9A.

FIGS. 9A and 9B illustrate an exemplary stabilization member 180' substantially identical to that shown in FIGS. 8A and 8B, except with a longer extension portion 184'. The stabilization members 180, 180' shown in FIGS. 8A-9B can have any length as needed for a particular procedure or for a use in a particular anatomy. For example, the stabilization members 180, 180' can have a length in the range of about 10 mm to about 35 mm, more preferably in the range of about 15 mm to about 30 mm, for example, about 17 mm, 18 mm, 19 mm, 20 mm, 21 mm, 22 mm, 23 mm, 24 mm, 25 mm, 26 mm, etc.

Figure 10A:
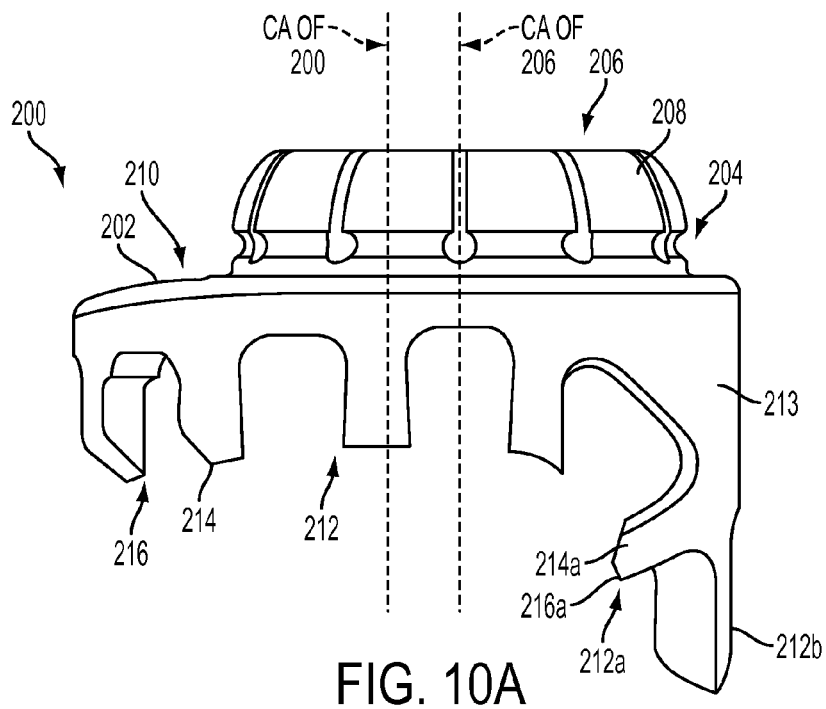
FIG. 10A is a side view of one embodiment of a stabilization member having an extension portion.
Figure 10B:
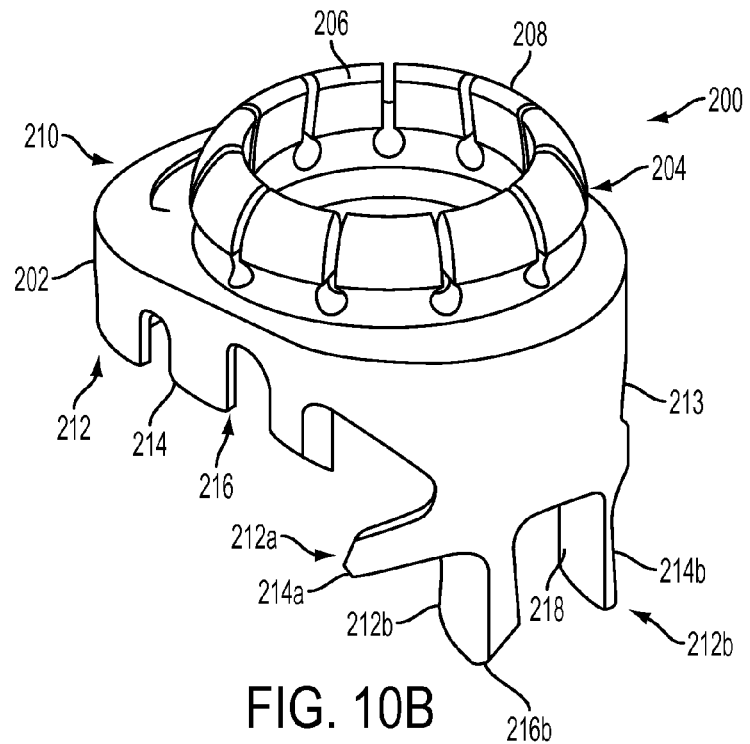
FIG. 10B is a perspective view of the stabilization member of FIG. 10A.

In another embodiment illustrated in FIGS. 10A and 10B, a stabilization member 200 is provided. The stabilization member 200 can be extended laterally such that a stabilizing plate portion 202 of the stabilization member 200 is substantially oblong and/or oval. Similar to the embodiments described above, the stabilization member 200 can have an elongate member receiving portion 204 with an opening 206 formed therethrough and a plurality of expandable arms 208 extending proximally therefrom in a substantially circular configuration for receiving a substantially spherical head of an elongate member. As shown, a central axis of the opening 206 can be offset from a central axis of the stabilization member 200. The stabilization member 200 can also have an extension portion 210.

The stabilizing plate portion 202 can have a plurality of bone engaging tines 212 extending distally therefrom around a perimeter thereof. In this embodiment, the bone engaging tines 212 can have an asymmetric configuration in which one or more of the tines have a length and/or angular configuration different than a length and/or angular configuration of at least one other of the tines 212. This can provide for better purchase within bone and can allow variable placement, for example, into the lamina or adjacent to a mammillary process. As shown, the stabilizing plate portion 202 can have an extension portion 213 extending distally from one lateral side thereof configured, for example, to extend into a pedicular valley. The extension portion 213 can have, for example, one or more bone engaging members extending therefrom that are disposed distally and angularly. As shown, two bone engaging tines 212a are angled relative to the other tines 212, and two bone engaging tines 212b are formed at a distal end of the extension portion 213 and are thus substantially greater in length than the other tines 212. The extension portion 213 can provide the stabilization member 200 with a more aggressive engagement into the bone and thus a more secure purchase therein.

The bone engaging tines 212 can be arranged in many different ways, and in the illustrated embodiment, the tines 212 can each terminate in such a way as to form an overall curved configuration relative to the stabilizing plate portion 202, as shown in FIG. 10A. The shorter tines 212 can have any desired shape and configuration, but in the illustrated embodiment, they have a configuration the same as that described above with an outer surface 214 angled toward a central axis of the stabilization member 200 and a bone piercing and/or penetrating tip 216 formed at the distal end. The angled tines 212a can have a non-angled outer surface 214a with angled bone piercing and/or penetrating tips 216a. Further, the longer tines 212b can have an angled inner surface 218 with a non-angled outer surface 214b and bone piercing and/or penetrating tips 216b at their distal end. The extension portion 213 can have a length from the stabilizing plate portion 202 in the range of about 10 mm to about 20 mm, more preferably in the range of about 13 mm to about 18 mm, for example about 15 mm. A width of the stabilization member can be the same as described above for the embodiment shown in FIGS. 8A-9B.

Figure 11A:
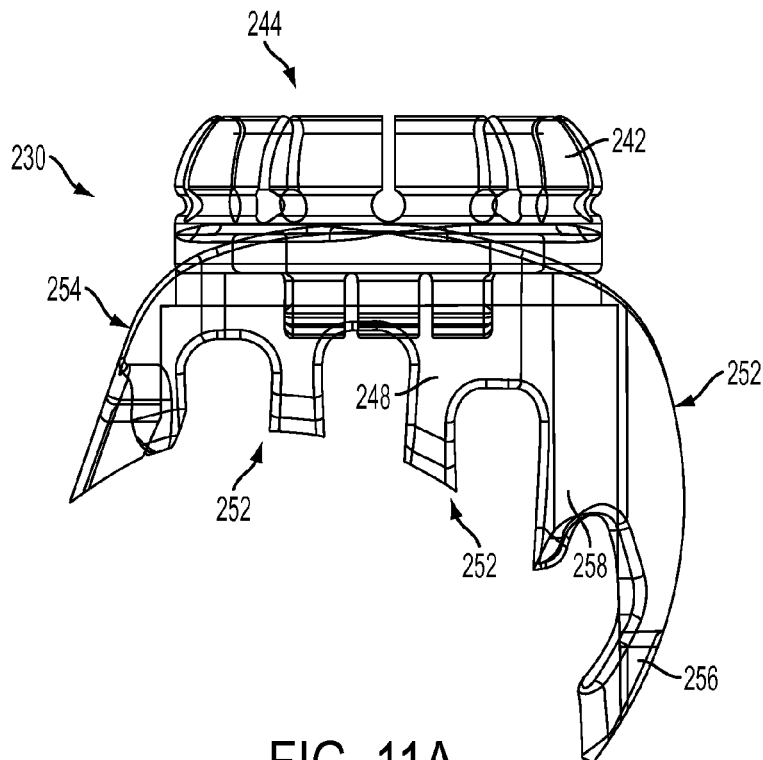
FIG. 11A is a side view of another embodiment of a stabilization member having a translatable portion.
Figure 11B:
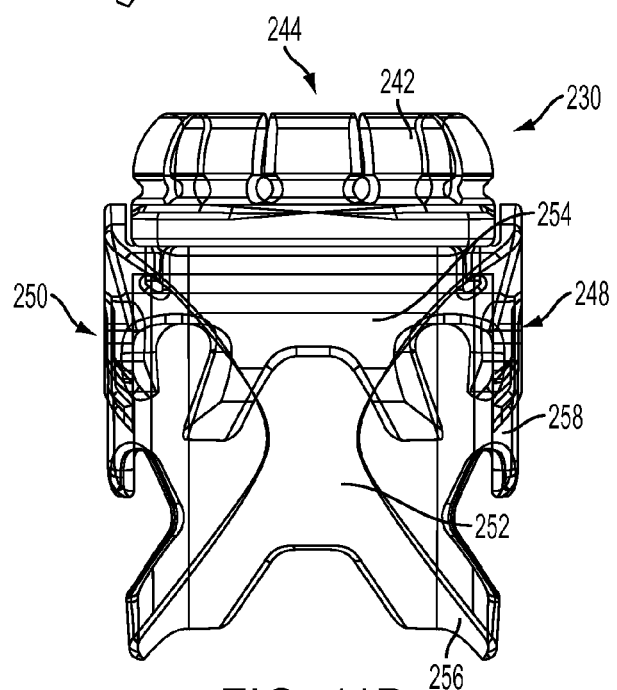
FIG. 11B is a front view of the embodiment of FIG. 11A.
Figure 11C:
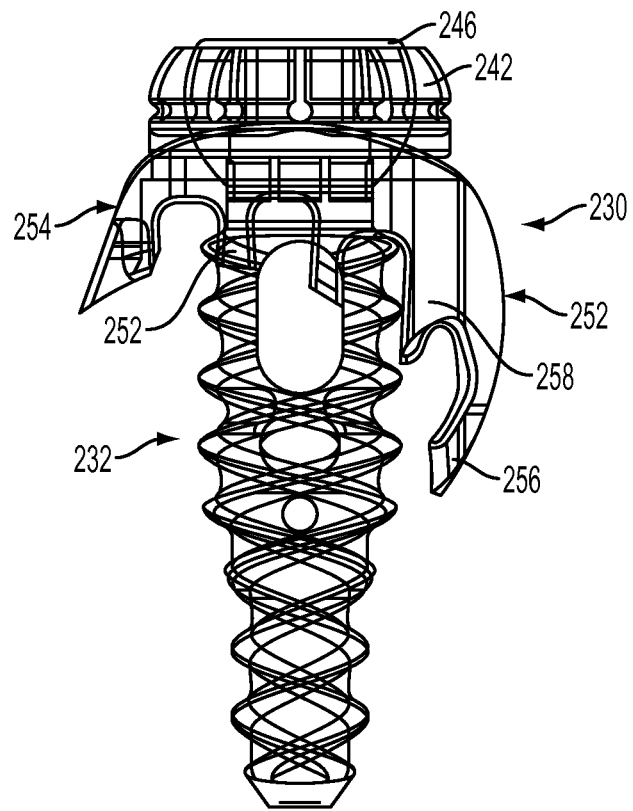
FIG. 11C is a side view of the embodiment of FIG. 11A having an elongate member disposed therein.
Figure 11D:
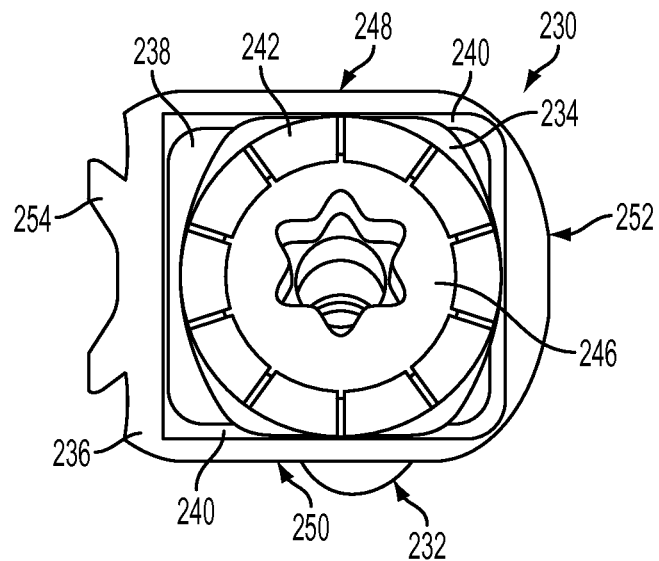
FIG. 11D is a top view of the embodiment of FIG. 11C.

A further embodiment of a stabilization member 230 is illustrated in FIGS. 11A-11D. In this embodiment, the stabilization member 230 can have a repositioning mechanism and/or adjustable coupling configured to allow translation of an elongate member 232 in at least one direction relative thereto. The stabilization member 230 can be extended laterally such that its length is longer than its width, and it can accommodate a movable translation plate 234, shown most clearly in FIG. 11D, to facilitate translation of the elongate member 232. A stabilizing plate portion 236 of the stabilization member 230 can have a substantially rectangular opening 238 formed therein to receive the translation plate 234 and can define rails 240 on which the translation plate 234 can slide. The translation plate 234 can therefore have a width substantially the same as the width of the stabilizing plate portion 236, but a length shorter than the length of the stabilizing plate portion 236 so that it can translate lengthwise. A plurality of expandable arms 242 can extend proximally from the translation plate 234 and can define an opening 244 for receiving a head 246 of the elongate member 232. A diameter of the opening 244 can be substantially the same as the width of the translation plate 234 and the stabilizing plate portion 236, as shown in FIG. 11D.

Four sidewalls can define an outer perimeter of the stabilizing plate portion 236 and can terminate distally in a plurality of bone engaging tines. Two opposing sidewalls 248, 250 can be symmetric and can have a number of different length tines 252 arranged in a curved configuration as shown in FIGS. 11A and 11C. The opposed symmetric sidewalls 248, 250 can extend proximally a distance above the stabilizing plate portion 236 in a curved configuration to define sidewalls for the rails. The other two opposing sidewalls 252, 254 can be asymmetric and can have asymmetric bone engaging tines formed at a distal end thereof. One of the asymmetric sidewalls 252 can extend distally in a curved configuration such that the sidewall 252 forms an arc outward from the stabilizing plate portion 236 and then inward toward a central axis of the stabilization member 234 terminating in two distal bone engaging tines 256 and two side bone engaging tines 258. The bone engaging tines 256 formed at a distal end of the sidewall 252 can have a length substantially greater than the lengths of the other bone engaging tines 252, 258. The other asymmetric sidewall 254 can extend distally at an angle relative to the stabilizing plate portion 236 such that the sidewall 254 is angled away from the central axis of the stabilization member 230, rather than being orthogonal to the central axis, as with the symmetric sidewalls 248, 250, or angled toward the central axis, as with the other asymmetric sidewall 252.

In use, the translation plate 234 coupled to the elongate member 232 can translate relative to the stabilizing plate portion 236 in a direction parallel with the opposing symmetric sidewalls 248, 250 or orthogonal to the opposing asymmetric sidewalls 252, 254. For example, in some embodiments, the translation plate 234 can translate by a distance in the range of about 5% to about 40% of a length of the stabilization member 230. In an embodiment in which the length of the stabilization member 230 is about 16 mm, the translation plate 234 can translate about 4 mm (about 25%) in each direction. As will be appreciate by those skilled in the art, the stabilization member 230 can have any length as needed for a particular procedure and/or to fit a particular anatomy.

Another exemplary embodiment of an implant 260 is illustrated in FIGS. 12A-12E. In this embodiment, the implant 260 can include a laterally extended stabilization member 262 configured to receive both an elongate member 264 and a fixation screw 266. A stabilizing plate portion 268 of the stabilization member 262 can be substantially oblong and/or oval. A first side 270 of the stabilizing plate portion 268 can have an opening 272 formed therethrough defined by a plurality of expandable arms 274 extending proximally from the stabilizing plate portion 268 and configured to receive a substantially spherical head 276 of the elongate member 264 therein. The opening 272 can be configured to allow polyaxial rotation of the elongate member 264 relative to the stabilization member 262. A second side 278 of the stabilizing plate portion 268 can have an opening 280 formed therethrough configured to receive the fixation screw 266. A diameter of the opening 280 can be smaller than a diameter of the opening 272. As with previous embodiments, a plurality of bone engaging tines 282 can extend distally from the stabilizing plate portion 268 around a perimeter of the stabilizing plate portion 268.

One or more bend zone regions 284 can be disposed between the first and second sides 270, 278. The bend zone regions 284 can be thinned portions of the stabilizing plate portion 268 that are flexible and thus able to be bent such that each of the first and second sides 270, 278 can be disposed at a different angle in bone relative to one another. This can allow the implant 260 to be more versatile and to more easily engage with a wider variety of bone surfaces and anatomies.

Any of the elongate members described herein can be disposed within the opening 280 in the first side 270 of the stabilizing plate portion 268. Further, while any type of elongate member can be used within the opening 272 in the second side 278 of the stabilizing plate portion 268, in the illustrated embodiment, the lamina fixation screw 266 is utilized. The fixation screw 266 can have a flattened head 286 with a shank 288 extending distally therefrom. The shank 288 can have a thread 290 disposed therearound and can have a diameter that decreases in a proximal to distal direction. The use of the fixation screw 266 with the elongate member 264 can provide a more secure and stable attachment to bone. For example, while the elongate member 264 is disposed within the facet joint, the fixation screw 266 can be disposed within the lamina to provide a more secure attachment for the elongate member 264. Further, the stabilizing plate portion 268 can be bent along its one or more bend zone regions 284 so that the stabilization member 262 can more closely form to the anatomy of the bone.

Figure 13A:
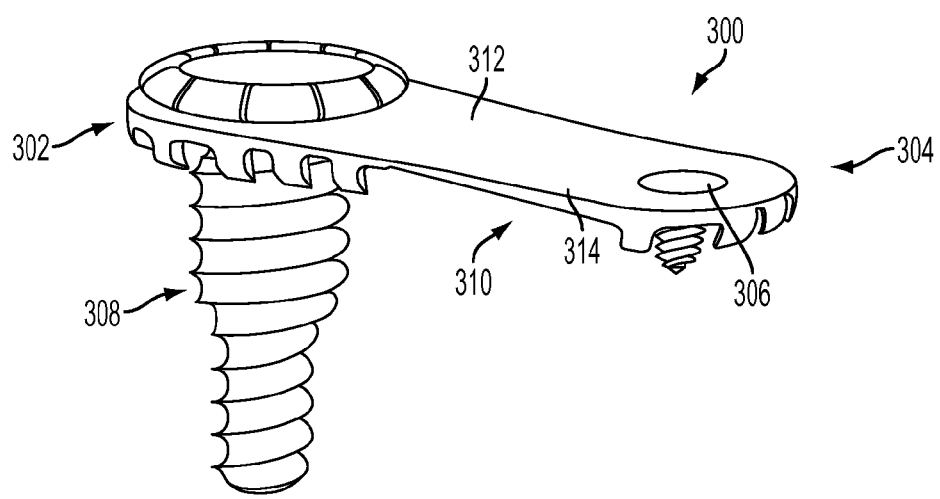
FIG. 13A is a perspective view of another embodiment of an implant having a lateral adjustment mechanism.
Figure 13B:
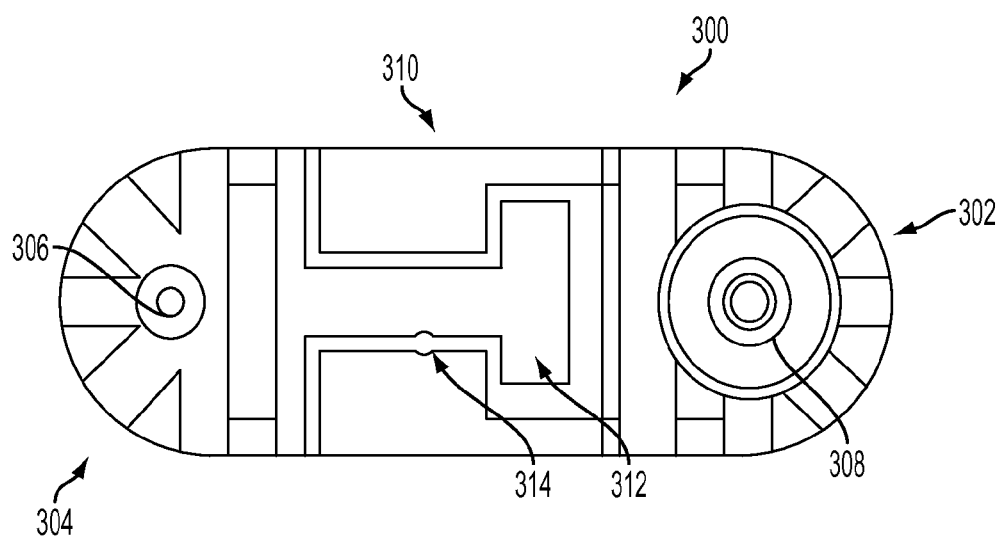
FIG. 13B is a bottom view of the implant of FIG. 13A.
Figure 14A:
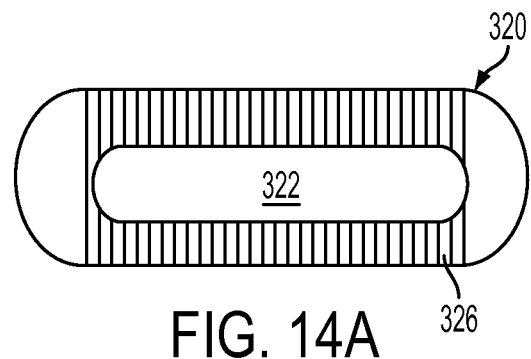
FIG. 14A is a top view of one embodiment of a stabilization member configured to allow lateral adjustment.
Figure 14B:
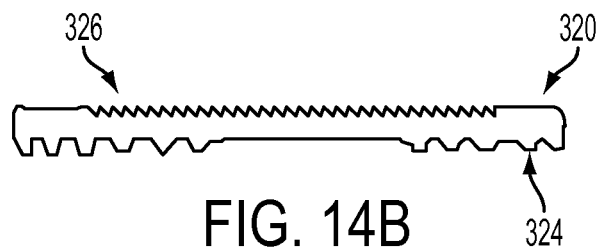
FIG. 14B is a side view of the stabilization member of FIG. 14A.
Figure 14C:
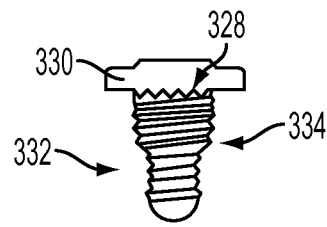
FIG. 14C is a side view of an elongate member configured to be inserted within the stabilization member of FIG. 14A.
Figure 14D:
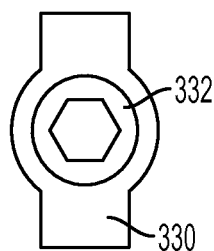
FIG. 14D is a top view of the elongate member of FIG. 14C.

Another embodiment of an implant similar to that in FIGS. 12A-12E, and having a repositioning mechanism and/or adjustable coupling associated therewith, is illustrated in FIGS. 13A and 13B. A stabilization member 300 is provided having first and second sides 302, 304, each side 302, 304 configured to receive one of a fixation screw 306 and an elongate member 308. In this case, however, a bend zone region 310 is in the form of a "T key" with one side 312 being in the shape of a T and the other side 314 having a complementary shape for receiving the T. The bend zone region 310 can be bendable, as well as laterally adjustable, and can thus be expanded laterally and/or bent to fit a particular anatomy. As will be appreciated by those skilled in the art, any shaped interlocking configuration can be used in the bend zone region 310 to facilitate lateral adjustment of the region.

FIGS. 14A-14D illustrate another embodiment of an implant having a repositioning mechanism and/or adjustable coupling. As shown, a stabilization member 320 is provided having a slotted opening 322 formed therethrough. A plurality of bone engaging members 324 can extend distally therefrom for engaging a bony surface, and a plurality of teeth 326 can be formed in a proximal surface thereof for engaging corresponding teeth in a head 330 of an elongate member 332, shown in FIG. 14C. The elongate member 332 can have a substantially flattened head 330 with a distal surface having a plurality of teeth 328 for engaging the teeth 326 formed in the proximal surface of the stabilization member 320. A shank 334 can extend distally from the head 330. When the elongate member 332 is disposed within the slotted opening 322 in the stabilization member 320, it can be moved laterally to a desired position along the member 320. Engagement between the teeth 326, 328 prevent further movement once positioned. In some embodiments, the stabilization member 320 can be bendable along its slotted opening 322 to facilitate attachment to a variety of bony surfaces and anatomies.

The above implant embodiments can be formed of any suitable material known in the art. A particular stabilization member and elongate member can be formed of the same material or of different materials. In addition, different portions of a particular stabilization member or elongate member can be formed of different materials. In some embodiments, the implant or a portion thereof can be formed from titanium or a titanium alloy, polyether ether ketone (PEEK), ceramic, 316 stainless steel, CoCr, trabecular metals, zirconia, crystalline hydroxyapatite, TCP, poly-lactic acid & poly-glycolic acid and blends thereof, etc. In other embodiments, the implant or a portion thereof, can be formed of Nitinol. The temperature characteristics of Nitinol can allow the stabilization member and/or the elongate member to expand or contract when disposed in bone to facilitate better placement and securement with a particular location, as well as to reduce loosening of the implant once implanted.

The various implant embodiments disclosed herein can generally be utilized to provide fixation and/or fusion to a facet joint. The various elongate members described herein can be delivered into a facet joint, and in some embodiments, can be anchored into the pedicle for added fixation. The various stabilization member embodiments described herein can be used to mechanically co-join the facet faces. An overview of facet joint anatomy and prior art methods of providing spinal fixation to a facet joint can be found in U.S. Patent Application No. 2008/0255622, filed on Apr. 13, 2007 and entitled "Facet Fixation and Fusion Screw and Washer Assembly and Method of Use," which is incorporated by reference in its entirety.

Figure 15A:
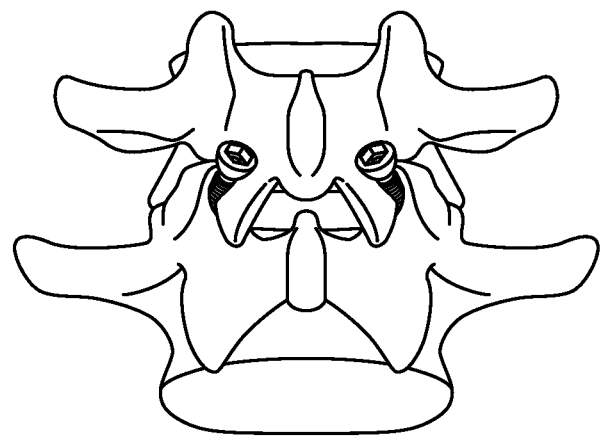
FIG. 15A is a perspective view of exemplary implants disposed within a facet joint in a trans-facet orientation.
Figure 15B:
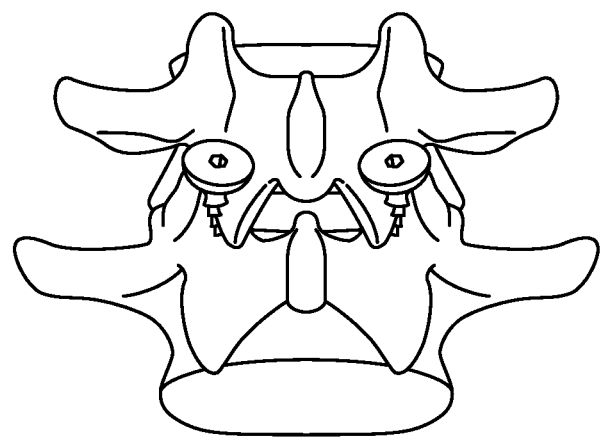
FIG. 15B is a perspective view of exemplary implants disposed within a facet joint in an intra-facet orientation.
Figure 15C:
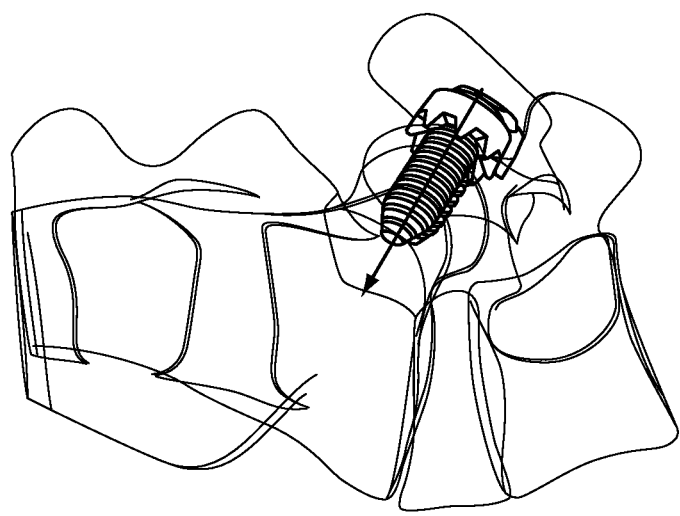
FIG. 15C illustrates a trajectory of an exemplary implant through the facet joint and into the pedicle.

In use, an exemplary elongate member coupled to an exemplary stabilization member can be provided for insertion into a facet joint. The elongate member and/or the stabilization member can optionally be packed with, formed from, or and/or coated with a bio-active fusion promoting composition. The insertion procedure can preferably be performed minimally invasively, although it can be performed using any surgical procedure now in use or yet to be. The elongate member and stabilization member can be delivered into and secured within and around the facet joint and pedicle in a number of ways. For example, in some embodiments, the implant can be inserted using various trajectories that start in intra-facet (between the facet faces) or trans-facet (through the facet faces) and subsequently pass close to the centroid of the pedicular bone that connects the vertebral body to the lamina. More particularly, the elongate member can be placed in between the facet faces in an intra-facet pedicular trajectory, as shown in FIG. 15B, or can be placed in a trans-facet trajectory, as shown in FIG. 15A. In other embodiments, the implant can be inserted using various trajectories that do not start within or pass through the facet joint but pass close to the centroid of the pedicular bone that connects the vertebral body to the lamina, including entry into the lateral aspect of that facet or entry directly into the pedicle. For example, the implant can be placed into the pedicle valley in a traditional pedicular trajectory, as shown in FIG. 15C, and/or it can placed into the mammillary process.

While there are a number of different ways in which rrthe implant can be delivered to the facet joint, in one embodiment, the stabilization member can be delivered to the facet joint first, before delivery of the elongate member. An opening can be formed within the patient and a guidewire can be inserted using fluoroscopy and other conventional techniques. Serial dilation can be performed to provide access through tissue to the facet joint. An opening for the elongate member can be drilled into, within, or near the facet joint at the desired insertion trajectory. The stabilization member can be delivered to the facet joint area for sizing, followed by awling of any securement features. The stabilization member can then be secured to the desired anatomy by piercing the bone with the bone engaging members. If the stabilization member has bending features, lateral extensions, or other additional securement features, they can be manipulated and/or utilized to provide additional engagement and stabilization. For example, a portion of the bone engaging members of the stabilization member can engage an outer portion of the facet of a first vertebra and another portion of the bone engaging members can engage an outer portion of the facet of a second, adjacent vertebra. The stabilization member can be bent around these portions and/or laterally adjusted to an appropriate length for engagement with these portions. Once the stabilization member is secured, the elongate member can be inserted through an opening within the stabilization member and into the predrilled opening within, through, or around the facet joint. In some embodiments, a set screw can be placed into an opening within a head of the elongate member to expand the head into tighter interlocking engagement with the stabilization member. In other embodiments, the stabilization member and the elongate member can be delivered to and implanted within or around the facet joint as a coupled implant using the above-described techniques.

The implants described herein can be used, for example, in facet volume restoration procedures and/or partial correction of coronal plane deformity (scoliosis) at one or more vertebral levels. This enables the implant to be used as a fusion device and permits deformity correction at one or more levels. Further, the implant can be used for thoracic spine facet joint fusion and deformity correction, and can also assist in deformity correction when used with mono-portal transforaminal lumbar interbody fusion (TLIF) and posterior lumbar interbody fusion (PLIF) to correct disc height lost, coronal deformity, and foraminal volume loss. The implants can further be used in other procedures such as posterior stabilization for an anterior lumbar interbody fusion (ALIF 360), reduction of low-grade spondylolisthesis, or terminal fusion of diseased and painful facet joints.

In some embodiments, a system or kit is provided and can include one or more of the exemplary implants, stabilization members, and/or elongate members described herein. In addition, the system or kit can include one or more tools that permit delivery and insertion, as well as some longitudinal distraction of the facet joint. Any of the stabilization member and elongate member embodiments disclosed herein can be included in such a system or kit and can be fully interchangeable with one another.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal implant, comprising:
  a cannulated elongate member having a first bone engaging portion with a first diameter and a second bone engaging portion with a second diameter disposed distal to the first bone engaging portion, the first bone engaging portion being configured for insertion into a facet joint and the second bone engaging portion being configured for insertion into a pedicle, at least one of the first and second bone engaging portions having at least one opening formed in a sidewall thereof and configured to receive an osteoconductive composition; and
  a stabilization member configured to seat the elongate member, the stabilization member having a first expandable portion configured to engage a proximal portion of the elongate member in a snap-fit configuration and a second bone engaging portion having a plurality of bone engaging tines extending therefrom, each bone engaging tine being angled toward a central axis of the elongate member,
  wherein the first diameter is greater than the second diameter.

2. The spinal implant of claim 1, wherein at least one of the first and second bone engaging portions has a plurality of openings formed in the sidewall thereof.

3. The spinal implant of claim 2, wherein each of the plurality of openings is a different shape.

4. The spinal implant of claim 1, wherein the elongate member includes a proximal head with a shank extending distally therefrom, the shank having a thread extending over at least a portion of thereof.

5. The spinal implant of claim 1, wherein the first expandable portion comprises a plurality of substantially flexible arms arranged in a circular configuration, each arm being separated from adjacent arms by a slit configured to allow expansion and contraction of the arms.

6. The spinal implant of claim 5, wherein the plurality of substantially flexible arms are configured to receive a proximal head of the elongate member and to allow rotation in all directions of the proximal head relative thereto.

7. The spinal implant of claim 1, wherein the stabilization member includes a lateral extension such that a central axis of the first expandable portion is offset from a central axis of the stabilization member.

8. The spinal implant of claim 7, wherein the lateral extension is configured to bend relative to the first expandable portion to conform to a bony surface adjacent to a facet joint as the elongate member is positioned within the facet joint.

9. A spinal implant, comprising:
  an elongate member having a proximal head and a bone engaging shank extending distally from the proximal head, the proximal head being configured for rotational movement in all directions within a stabilization member, the shank further having a thread extending over at least a portion thereof, and a proximal portion with a first major diameter and a distal portion with a second major diameter, wherein the first major diameter is greater than the second major diameter; and
  a stabilization member configured to seat the elongate member, the stabilization member having a plurality of expandable arms extending proximally therefrom, the expandable arms configured to receive the proximal head in a snap fit connection.

10. The spinal implant of claim 9, the shank having at least first and second openings formed in a sidewall thereof and being configured to receive an osteoconductive composition, wherein the first and second openings are disposed along a longitudinal axis of the elongate member;
wherein at least one of the first and second openings are foamed the portion of the shank having the thread.

11. The spinal implant of claim 10, wherein the first and second openings have different shapes.

12. The spinal implant of claim 9, wherein the stabilization member includes a stabilizing plate portion having a plurality of bone engaging tines extending distally therefrom for piercing bone.

13. The spinal implant of claim 12, wherein the stabilizing plate portion has a length extending between first and second opposed sides and a width extending between third and fourth opposed sides, wherein the length is greater than the width.

14. The spinal implant of claim 13, wherein the stabilizing plate portion includes an extension member extending distally from one of the first and second opposed sides, the extension member having a length greater than a length of the plurality of bone engaging tines.

15. The spinal implant of claim 13, wherein the stabilizing plate portion includes at least one bendable region disposed thereon such that the stabilizing plate portion is bendable along a line orthogonal to the length of the stabilizing plate portion.

16. The spinal implant of claim 13, wherein the stabilization member further includes a translation plate disposed adjacent to the stabilizing plate portion and having a plurality of expandable arms extending proximally therefrom configured to receive the proximal head of the elongate member and to allow rotational movement of the proximal head in all directions relative to the stabilization member.

17. The spinal implant of claim 16, wherein the translation plate is configured to translate laterally with the elongate member relative to the stabilizing plate portion along the length of the stabilizing plate portion.

18. The spinal implant of claim 13, wherein the expandable arms extend proximally from the stabilizing plate portion and define a first opening disposed adjacent to one of the first side and the second side and offset from a central axis of the stabilizing plate portion.

19. The spinal implant of claim 18, further comprising a second elongate member, and wherein the stabilizing plate portion includes a second opening formed on the first or second side opposite to that of the first opening, the second opening configured to receive the second elongate member therethrough.

20. The spinal implant of claim 19, wherein the second elongate member is a lamina screw configured to engage a lamina while the elongate member is engaged within a facet joint.

21. The spinal implant of claim 13, wherein the stabilizing plate portion includes a first portion and a second portion, the first and second portions being coupled together by an adjustable coupling.

22. The spinal implant of claim 21, wherein the adjustable coupling is configured to allow translation of the first portion relative to the second portion and bending of the first portion relative to the second portion.

23. A method of implanting a spinal implant, comprising:
providing an elongate member having a first bone engaging portion and a second bone engaging portion, at least one of the first and second bone engaging portions having at least one opening formed therein for receiving an osteoconductive composition;
packing an osteoconductive composition into the opening;
surgically delivering the elongate member into a vertebra such that the first bone engaging portion is disposed within a facet joint and the second bone engaging portion is disposed within a pedicle;
penetrating a stabilization member, coupled to the elongate member, into a bony portion of a vertebra;
wherein penetrating a stabilization member, coupled to the elongate member, into a bony portion of a vertebra further comprises engaging a bony portion of a vertebra adjacent to the facet joint in which the elongate member is disposed; and
surgically delivering a lamina screw to a vertebral lamina through an opening in the stabilization member to provide additional stabilization for the elongate member disposed within the facet joint.

24. The method of claim 23, further comprising bending the stabilization member to engage a bony portion of a vertebra adjacent to the facet joint in which the elongate member is disposed.

25. The method of claim 23, further comprising delivering a first spinal implant to a first facet joint and a second spinal implant to a second, corresponding facet joint at the same level of a spine.

26. The method of claim 23, wherein the surgically delivering step is conducted in a minimally invasive surgical procedure.

* * * * *